United States Patent
Barnes et al.

(10) Patent No.: US 6,375,926 B1
(45) Date of Patent: Apr. 23, 2002

(54) LABELLED ELASTASE INHIBITORS

(75) Inventors: Karen Jane Barnes, Chesham; Gary Robert Bower, Aylesbury; Alan Michael Forster, High Wycombe; Peter Knox, Chalfont St Giles; Marivi Mendizabal, London; Anthony Eamon Storey, Amersham, all of (GB)

(73) Assignee: Amersham International PLC, Little Chalfont Bucks ( * ) Notice: Subject to any disclaimer, the term of this patent is extended or adjusted under 35 U.S.C. 154(b) by 0 days.

(21) Appl. No.: 09/254,541

(22) PCT Filed: Sep. 10, 1997

(86) PCT No.: PCT/GB97/02467

§ 371 Date: May 16, 2000

§ 102(e) Date: May 16, 2000

(87) PCT Pub. No.: WO98/10800

PCT Pub. Date: Mar. 19, 1998

(30) Foreign Application Priority Data

Sep. 16, 1996 (EP) ............................................ 96306718

(51) Int. Cl.$^7$ ........................ A61K 51/00; A61M 36/14
(52) U.S. Cl. ...................... 424/1.65; 424/1.11; 548/952
(58) Field of Search ............................... 424/1.11, 1.65, 424/9.1, 1.37; 548/950, 951, 952

(56) References Cited

U.S. PATENT DOCUMENTS 5,616,692 A * 4/1997 Fritzberg et al. .......... 530/391.5
5,948,624 A * 9/1999 Rothschild et al. ............ 435/6

FOREIGN PATENT DOCUMENTS

| WO | WO 93/21209 | 10/1993 |
| WO | WO 93/24519 | 12/1993 |
| WO | WO 96/23812 | 8/1996 |

OTHER PUBLICATIONS

Underwood et al., "Mechanism of Inhibition of Human Leucocyte Elastase by β–Lactams. 3. Use of Electrospray Ionization Mass Spectrometry and Two–Dimensional NMR Techniques To Identify β–Lactam–Derived E–I Complexes," *Biochemistry*, 34(44):14344–14355 (1995).

Rusckowski et al., "A New Technetium–99m–Peptide For Inflammation Imaging," 43rd Annual Meeting of the Society of Nuclear Medicine, Denver, Colorado, USA, Jun. 3–5 (1996) and *Journal of Nuclear Medicine*, 37(5 SUPPL.):p152P (1996).

Doherty et al., "Chemical, biochemical, pharmacokinetic, and biological properties of L–680,833: A potent, orally active monocyclic β–lactam inhibitor of human polymorphonuclear leukocyte elastase," *Proc. Natl. Acad. Sci., USA*, 90:8727–8731 (Sep., 1993).

Blaszczak et al., "Radioiododestannylation. Convenient Synthesis of a Stable Penicillin Derivative For Rapid Penicillin Binding Protein (PBP) Assay," *J. Labelled Compd. Radiopharm.*, 27(4):401–406 (1989).

* cited by examiner

Primary Examiner—Dameron L. Jones
(74) Attorney, Agent, or Firm—Marshall, Gerstein, & Borun.

(57) ABSTRACT

A human leucocyte elastase (HLE) inhibitor labelled with a detector moiety where the inhibitor is synthetic and has a molecular weight of less than 2000, is useful for the diagnostic imaging of sites of inflammation of infection in vivo, for labelling leucocytes in vitro, or for radiotherapy of rthritis. The HLE inhibitor is preferably a β-lactam or an azetidinone.

14 Claims, No Drawings

LABELLED ELASTASE INHIBITORS

This a 371 of PCT/GB97/02467, filed on Sep. 10, 1997.

The present invention relates to a class of compounds useful in the diagnosis or radiotherapy of infection, inflammation or thrombi, pharmaceutical formulations containing them, their use in diagnosis of disease and methods for their preparation.

Diagnostic imaging of infection or inflammation in clinical practice typically uses either the radiopharmaceutical $^{67}$Ga citrate, or radiolabelled white blood cells (leucocytes) since leucocytes are known to accumulate at sites of infection/inflammation. $^{111}$In or $^{99m}$Tc are the radioisotopes normally used to label leucocytes.

Labelled leucocytes have become the method of choice in current clinical practice for the diagnostic imaging of sites of infection/inflammation. With the favourable imaging characteristics of $^{99m}$Tc, the specificity of labelled leucocytes and good background clearance, this approach lends itself to the diagnosis of gut lesions such as inflammatory bowel disease or appendicitis. Such diseases cannot be diagnosed with non-specific agents due to the high gut background levels. The problem with the ex-vivo labelled leucocyte approach is that the current cell labelling agents used are non-specific. This means that the leucocytes have to be first separated from the excess red blood cells in blood taken from the patient to be imaged. The cell separation is a labour-intensive operation which requires a skilled operator to achieve efficient separation without compromising white cell integrity. There is also the intrinsic hazard associated with manipulation of blood samples. There has therefore been considerable interest in the field in developing an agent which could be used to image sites of infection which does not require this onerous cell separation prior to labelling and administration to the patient.

Human leucocyte elastase (HLE) is a powerful endopeptidase enzyme capable of hydrolysing amide bonds in a variety of proteins and peptides, including the structural proteins elastin, collagen and fibronectin [R L Stein et al, Ann. Rep. Med. Chem., 20, 237 (1985); P D Edwards and P R Bernstein, Med. Chem. Rev., 14, 127 (1994)]. At sites of infection or inflammation HLE is released by the activated leucocytes and causes tissue destruction. It is also known that leucocytes accumulate in thrombi and that elastase is released during blood coagulation. The released elastase has been shown to be important in fibrinogenlysis [E. F. Plow, J. Clin. Invest., 69, 564–572 (1982)].

EP 0595557 A1 (Merck) discloses that the following compounds are useful as HLE inhibitors for the treatment of inflammatory pathologies such as emphysema or rheumatoid arthritis:

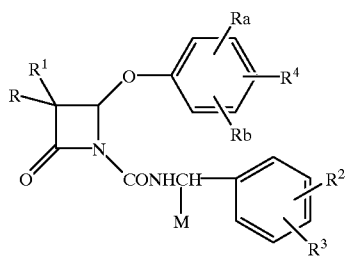

where: R is $C_{1-6}$ alkyl;
$R^1$ is $C_{1-6}$ alkyl or $C_{1-6}$ alkoxy-$C_{1-6}$ alkyl;
M is H, $C_{1-6}$ alkyl, hydroxyalkyl, alkoxyalkyl, haloalkyl or $C_{2-6}$ alkenyl;
Ra and Rb are H, Hal, OH, Ph, COOH or $C_{1-6}$ alkyl, alkoxy or ester;
$R^2$ and $R^3$ are H, Hal, COOH, Ph, OH, CN, amino, $C_{1-6}$ alkyl, alkoxy or ester, or amide
$R^4$ is amide or ester with an optional alkyl spacer group.

Radio labelled HLE inhibitors have been little studied. Moser et al. [Am. J. Med., 84 (Suppl.6A), 70 (1988)] report that $^{131}$I-labelled $\alpha_1$-antitrypsin persists in the human lung for up to one week post injection with little or no uptake in the liver or spleen. The paper does not, however, discuss potential applications of radiolabelled ($\alpha$-antitrypsin. A tritium-labelled synthetic HLE inhibitor has been used to study the pharmacokinetics of the HLE inhibitor in rats and monkeys [J. B. Doherty et al, Proc. Nat. Acad. Sci. USA, 90, 8727–31 (1993)]. A $^{13}$C-labelled synthetic HLE inhibitor has been prepared to study the interaction of the inhibitor with HLE in vitro [B. G. Green et al, Biochem. 34, 14331–14355 (1995)]. Neither publication discloses the use of labelled HLE inhibitors for diagnostic imaging of infection, inflammation or thrombi nor are $^3$H or $^{13}$C suitable labelling moieties for external diagnostic imaging. Rusckowski et al [J. Nucl. Med., abstract P667 (1996)] report that a genetically engineered protein inhibitor of HLE named EPI-hNE-2 (molecular weight 6759) can be radiolabelled with $^{99m}$Tc via a bifunctional chelate. The radiolabelled protein is reported to show some uptake in a mouse infection model. EPI-hNE-2 is an oligopeptide and could suffer from the same immunogenic problems as Fab' or larger fragments of antibodies. Furthermore, the size of the molecule limits migration across cell membranes (e.g. those of granulocytes), hence intracellular HLE would not be targeted using this approach.

Blaszczak et al [J. Lab. Comp. Radiopharm., 27, 401–406 (1989)] have described the preparation of $^{125}$I-radiolabelled penicillin V (i.e. a bicyclic $\beta$-lactam) for use in the in vitro assay of penicillin binding protein. There is no suggestion in the paper of in vivo imaging applications and $^{125}$I would not be a preferred radioisotope for external imaging.

It has now been discovered that labelled synthetic HLE inhibitors are useful in the detection of sites of infection or inflammation. Use of a synthetic as opposed to a proteinaceous or polypeptide inhibitor has the significant advantages that the chemical nature of the agent can be fully defined, and potential concerns over immunogenicity are avoided. In addition the position of the label is known unambiguously, and unlike chemotactic peptides or interleukins, the labelled elastase inhibitor is not required to be of very high specific activity because there is an excess of elastase present both within granulocytes and at sites of infection/inflammation. The labelled HLE inhibitors are also useful in the detection of thrombi.

Thus the present invention relates to diagnostic agents for the detection of sites of infection or inflammation or thrombi in the human body. The agents comprise a synthetic human leucocyte elastase (HLE) inhibitor which has a molecular weight of less than 2000 Daltons and is labelled with a detectable moiety suitable for external imaging (e.g. by scintigraphy or MRI), such as a radionuclide or a paramagnetic metal ion. The agent acts by targeting HLE either within leucocytes (in vivo or in vitro), or at sites of HLE release such as sites of infection, inflammation or thrombi. Radiolabelled HLE inhibitors have been shown to selectively label human granulocytes in vitro and to target sites of infection/inflammation in vivo in an animal model of this pathology.

The "detectable moiety" is a substance suitable for external imaging after human administration such as a radionuclide which emits radiation that can penetrate soft tissue; a paramagnetic moiety as a contrast agent for MRI (e.g. certain metal ions such as gadolinium(III), or manganese (II)); a radiopaque moiety such as Iopamidol for X-ray contrast imaging (computer assisted tomography ) or an ultrasound contrast agent. Preferably, the detectable moiety is a radionuclide which is either a positron emitter (such as $^{18}$F, $^{11}$C, $^{15}$O, $^{13}$N, $^{68}$Ga or $^{64}$Cu) or a γ-emitter such as $^{123}$I, $^{99m}$Tc, $^{111}$In, $^{113}$mIn or $^{67}$Ga. Most preferred radionuclides are γ-emitters, especially $^{123}$I and $^{99m}$Tc. $^{3}$H and $^{14}$C do not have radioactive emissions suitable for external imaging and are therefore outside the scope of the present invention. It is also envisaged that certain radionuclides will confer useful radiotherapeutic properties on the labelled HLE inhibitors. Thus for example $^{90}$Y, $^{89}$Sr, $^{186}$Re, $^{188}$Re, $^{125}$I or $^{131}$I labelled HLE inhibitors could be used in the treatment of rheumatoid arthritis and other bone infections/inflammations. In such applications the therapeutic effect would be due to the local targeted radioactive dose delivered to specific cells, as opposed to any pharmacological effect due to the inhibitor. Whichever detectable moiety is chosen, it is strongly preferred that it is bound to the synthetic HLE inhibitor in such a way that it does not undergo facile metabolism in blood (in vivo or in vitro) with the result that the biodistribution of the detectable moiety no longer reflects that of the HLE inhibitor.

The data presented herein demonstrate that radiolabelled synthetic HLE inhibitors offer a novel and convenient method for targeting sites of infection/inflammation or thrombosis. The mechanism is believed to involve binding to HLE present within circulating granulocytes in the bloodstream (which then concentrate at the site of pathology), or binding to free, extracellular HLE released at sites of pathology. Such a directly-injectable infection/inflammation imaging compound offers significant advantages over existing and proposed radiopharmaceuticals. The specificity for HLE means that the agents should, like ex vivo labelled leucocytes, be capable of imaging lesions associated with leucocyte infiltration such as appendicitis or inflammatory bowel disease. Use of a relatively small synthetic molecule means that the background clearance problems associated with macromolecules are avoided, and substituents can readily be varied in a controlled manner to adjust lipophilicity, plasma protein binding and rate of clearance.

The following classes of synthetic HLE inhibitor with a molecular weight of less than 2000 are suitable for the present invention:

Short chain (3–5 mer) peptides and peptide analogues (e.g. trifluoroacetyl peptides), hydrophobic inhibitors (e.g. elasnin and synthetic analogues).

Inhibitors against the active site histidine (e.g. peptide chloromethyl ketones).

Covalent inhibitors (e.g. peptide aldehydes, peptide ketones, halomethylketones, peptide boronic acids) and acylating agents (sulphonyl fluorides, aminoalkyl phosphono fluoridates, azapeptide nitrophenyl esters, activated carbamates and latent isocyanates, benzoxazin-4-ones, 3-alkoxyl-4-chloroisocoumarins, isatoic anhydrides, acyl saccharins).

Mechanism based inhibitors (e.g. chloropyrones and chloroisocoumarins, 7-amino-4-chloroisocoumarins, ynenol lactones and β-lactams).

Preferred HLE inhibitors for use in the present invention are the mechanism-based inhibitors, especially β-lactams which can be monocyclic (i.e. azetidinones) or have more than one fused ring (such as penicillins, cephalosporins or clavulanic acid analogues) and ynenol lactones. Most preferred are β-lactams, especially monocyclic β-lactams (i.e. azetidinones).

Preferred β-lactams are of formula:

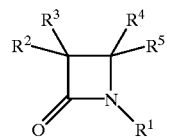

Where $R^1$ is $R^8$, $XR^8$, $(CRR)_n(C=X)R^8$ or $(C=X)NR^8_2$
X is O or S
n is 0–3.
$R^8$ is H, OH, a substituted or unsubstituted $C_{3-12}$ carbocyclic or heterocyclic ring which may be saturated or unsaturated, $C_{1-10}$ alkyl, $C_{3-12}$ aryl, $C_{4-12}$ alkylaryl, $C_{2-10}$ alkenyl, $C_{2-10}$ alkynyl, $C_{1-10}$ alkoxy, $C_{1-10}$ alkoxyalkyl, $C_{1-10}$ hydroxyalkyl, $C_{1-10}$ aminoalkyl, $C_{1-10}$ perfluoroalkyl, $C_{1-10}$ haloalkyl, $C_{1-10}$ carboxyalkyl, $C_{1-10}$ amidoalkyl or $C_{1-10}$ ketoalkyl.
$R^2$, $R^3$ are the same or different and each H, $C_{1-4}$ alkyl, $C_{2-4}$ alkenyl, $C_{2-4}$ alkynyl, $C_{1-4}$ alkoxyalkyl, $C_{1-4}$ hydroxyalkyl, $C_{1-4}$ aminoalkyl, $C_{1-4}$ perfluoroalkyl, $C_{1-4}$ haloalkyl, Hal, $C_{1-4}$ carboxyalkyl, OR, SR, NRR $(CH_2)_n$CONRR, NR(CO)R or $(CH_2)_n CO_2 R$.
$R^4$ is a leaving group chosen from Hal, $XR^8$, $X(C=X)R^8$, $OSOR^8$, $OSO_2R^8$ $OSO_2$Hal, $SOR^8$ $SO_2R^8$ $SO_2NR^8_2$ $NRSO_2R$, $(C=X)R^8$, $(C=X)NR^8_2$, $(C=X)R^8$, $NO_2$, CN, $PO_nR^8_2$ or $XC_6H_{4-n}Y_n$
Y is the same or different and is R, $NO_2$, Hal, $CONR^8_2$, $SO_2NR^8_2$ or $CO_2R$.
$R^5$ is R or $R^4$
R is the same or different and is H, $C_{1-4}$ alkyl, $C_{2-4}$ alkenyl, $C_{2-4}$ alkynyl, $C_{1-4}$ alkoxy, $C_{1-4}$ alkoxyalkyl, $C_{1-4}$ hydroxyalkyl, $C_{1-4}$ aminoalkyl, $C_{1-4}$ perfluoroalkyl, $C_{1-4}$ haloalkyl or $C_{1-4}$ carboxyalkyl.
whereby two or more of the groups $R^1$, $R^2$, $R^3$, $R^4$ and $R_5$ may be combined to form a substituted or unsubstituted carbocyclic or heterocyclic ring which may be saturated or unsaturated,
characterised in that the β-lactam contains or has covalently bonded thereto at least one detectable moiety, and with the proviso that when $R^4$ is $XR^8$, X is S and $R^1$ and $R^4$ are combined to form a cyclic carboxyalkyl group, then the detectable moiety is not $^{125}$I.

Preferred azetidinones are of formula:

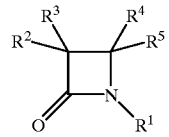

Where $R^1$ is $R^8$, $XR^8$, $(CRR)_n(C=X)R^8$ or $(C=X)NR^8_2$
X is O or S
n is 0–3.
$R^8$ is H, OH, a substituted or unsubstituted $C_{3-12}$ carbocyclic or heterocyclic ring which may be saturated or unsaturated, $C_{1-10}$ alkyl, $C_{3-12}$ aryl, $C_{4-12}$ alkyiaryl, $C_{2-10}$ alkenyl, $C_{2-10}$ alkynyl, $C_{1-10}$ alkoxy, $C_{1-10}$ alkoxyalkyl, $C_{1-10}$ hydroxyalkyl, $C_{1-10}$ aminoalkyl, $C_{1-10}$ perfluoroalkyl, $C_{1-10}$ haloalkyl, $C_{1-10}$ carboxyalkyl, $C_{1-10}$ amidoalkyl or $C_{1-10}$ ketoalkyl.
$R^2$, $R^3$ are the same or different and each H, $C_{1-4}$ alkyl, $C_{2-4}$ alkenyl, $C_{2-4}$ alkynyl, $C_{1-4}$ alkoxyalkyl, $C_{1-4}$ hydroxyalkyl, $C_{1-4}$ aminoalkyl, $C_{1-4}$ perfluoroalkyl, $C_{1-4}$ haloalkyl, Hal, $C_{1-4}$ carboxyalkyl, OR, SR, NRR $(CH_2)_nCONRR$, $NR(CO)R$ or $(CH_2)_nCO_2R$.

$R^4$ is a leaving group chosen from Hal, $XR^8$, $X(C=X)R^8$, $OSOR^8$, $OSO_2R^8$ $OSO_2Hal$, $SOR^8$ $SO_2R^8$, $SO_2NR^8_2$ $NRSO_2R$, $(C=X)R^8$, $(C=X)NR^8_2$, $(C=X)R^8$, $NO_2$, CN, $PO_nR^8_2$ or $XC_6H_{4-n}Y_n$ Y is the same or different and is R, $NO_2$, Hal, $CONR^8_2$, $SO_2NR^8_2$ or $CO_2R$.

$R^5$ is R or $R^4$

R is the same or different and is H, $C_{1-4}$ alkyl, $C_{2-4}$ alkenyl, $C_{2-4}$ alkynyl, $C_{1-4}$ alkoxy, $C_{1-4}$ alkoxyalkyl, $C_{1-4}$ hydroxyalkyl, $C_{1-4}$ aminoalkyl, $C_{1-4}$ perfluoroalkyl, $C_{1-4}$ haloalkyl or $C_{1-4}$ carboxyalkyl.

characterised in that the azetidinone contains or has covalently
bonded thereto at least one detectable moiety.

Attachment of the detectable moiety at the $R^4$ position is least preferred since this group is believed to be lost from the β-lactam as a consequence of covalent binding to the active site of the elastase enzyme. Groups $R^2$ and $R^3$ on the β-lactam are responsible for binding to the $S_1$ site on the enzyme, and literature evidence suggests that these groups need to be relatively small (e.g. the size of an ethyl moiety). Hence it is likely that only a limited range of detectable moieties could be successfully attached at the $R^2/R^3$ positions. The detectable moiety is therefore most preferably attached at the $R^1$ position of the β-lactam or azetidinone.

Preferred $R^1$ groups are those of formula:

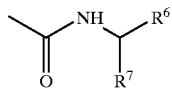

where $R^6$ is an optionally substituted alkyl or phenyl group to which the detectable moiety is attached and $R^7$ is H or a $C_{1-6}$ alkyl group.

When the detectable moiety is a radioactive or paramagnetic metal the metal is always chelated, i.e. a chelate-HLE inhibitor conjugate is used. Metal complexes of the HLE inhibitor alone (i.e. HLE inhibitors without at least one substituent which is designed to coordinate to metal atoms) are not part of the present invention. The term chelate-HLE conjugate covers the situations where the chelating agent is attached as a discrete chemical entity (i.e. as a single substituent on the HLE inhibitor), and when two or more metal donor atoms are attached as substituents at different positions on the HLE molecule. The chelate-HLE inhibitor conjugate is complexed with metal ions (such as technetium, gadolinium or yttrium) giving a metal complex of the chelating agent which is linked to the synthetic HLE inhibitor. The chelating agent is preferably polydentate and/or macrocyclic so that a stable metal complex is formed which can survive challenge by endogenous competing ligands for the metal in vivo such as transferrin or plasma proteins. When intracellular HLE is the target, the metal complex is preferably neutral since this facilitates transport of the labelled inhibitor conjugate across cell membranes such as those of granulocytes. When extracellular HLE released at sites of infection/inflammation or thrombi is the target then membrane permeability is of less importance and a charged metal complex may be desirable to facilitate background clearance. The metal complex should also preferably be of low lipophilicity (since high lipophilicity is often related to non-specific uptake), and exhibit low plasma protein binding (PPB) since plasma-bound label again contributes to undesirable high, non-specific blood background for the imaging agent.

Examples of suitable chelating agents for technetium are diaminedioximes (U.S. Pat. No. 4,615,876) or such ligands incorporating amide donors (WO 94/08949); the tetradentate ligands of WO 94/22816; diaminedithiols, tetraamines or dithiosemicarbazones. Stable technetium complexes are also formed with macrocyclic amine or amide ligands such as cyclam, oxocyclam (which forms a neutral technetium complex) or dioxocyclam. Suitable ligands for indium, yttrium and gadolinium are described in Sandoz WO 91/01144, preferred are macrocyclic aminocarboxylate and aminophosphonic acid ligands. Non-ionic (i.e. neutral) metal complexes of gadolinium are known and examples are described in U.S. Pat. No. 4,885,363.

When the detectable moiety is a radioactive isotope of iodine the radioiodine atom is preferably attached via a direct covalent bond to an aromatic ring such as a benzene ring, or a vinyl group since it is known that iodine atoms bound to saturated aliphatic systems are prone to in vivo metabolism and hence loss of the detectable moiety.

The compounds of the present invention may be prepared as follows:

When the detectable moiety is radioactive iodine, the $R^{1-5}$ group is chosen to include either a non-radioactive halogen atom (to permit radioiodine exchange), an activated aryl ring (e.g. a phenol group) or an organometallic precursor compound such as a trialkyltin, trialkylsilyl or other such moiety known to those skilled in the art. Examples of suitable $R^{1-5}$ groups to which radioactive iodine can be attached are given below:

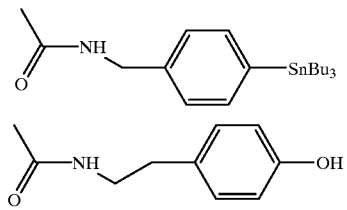

Both contain substituents which permit facile radioiodine substitution onto the aromatic ring. Alternative substituents containing radioactive iodine can be synthesised by direct iodination via radiohalogen

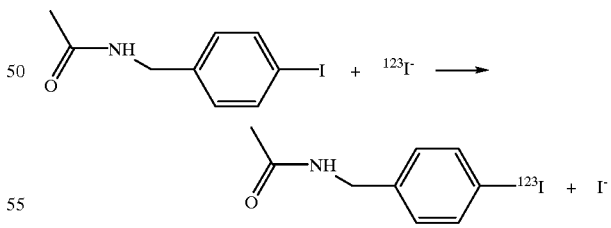

When the detectable moiety is a radioactive or paramagnetic metal ion the metal is preferably attached as a metal complex, i.e. a chelating agent is attached to the synthetic HLE inhibitor giving a chelate-HLE inhibitor conjugate. Such chelate-HLE inhibitor conjugates can be prepared using the bifunctional chelate approach. Thus it is well known to prepare chelating agents which have attached thereto a functional group ("bifunctional chelates"). Functional groups which have been attached to chelating agents include: amine, thiocyanate, maleimide and active ester such as N-hydroxysuccinimide. Such bifunctional chelates can be reacted with suitable functional groups on the HLE inhibitor to form the desired conjugate. Examples of chelate-amine conjugates for diaminedioxime ligands are given in WO 95119187. In the particular case of β-lactams, a chelating agent can be attached at the $R_1$ position as follows. First a chelate-amine conjugate is converted to a chelate-isocyanate conjugate using phosgene, trichloromethylchloroformate or similar. The chelating agent may optionally be protected with protecting groups known to those skilled in the art. The resulting chelate-NCO (isocyanate) conjugate can then be reacted with the amine NH of an azetidinone ring secondary amine giving a chelating agent attached at $R_1$ via a urea linkage. Similarly, a chelate-amine conjugate can be converted to a chelating agent with a pendant isothiocyanate group (as e.g. described in U.S. Pat. No. 5006643 or WO 91/01144) and then reacted with an azetidinone to give a chelating agent-azetidinone conjugate linked via a thiourea bond. Alternatively, reaction of a chelate-active ester conjugate with the amine NH of an azetidinone ring would give a chelate-azetidinone conjugate linked via an amide bond. A further approach to an amide-linked conjugate would be to couple the amine group of an chelate-amine conjugate to the pendant carboxyl group of a carboxyl-functionalised azetidinone. Persons skilled in the art will recognise that many alternative syntheses of chelate-HLE inhibitor conjugates are possible based on this disclosure.

The present invention also relates to kits for the preparation of synthetic HLE inhibitors labelled with a detectable moiety. The kits are designed to give sterile products suitable for human administration, e.g. via injection into the bloodstream. Possible embodiments are discussed below. When the detectable moiety is $^{99m}Tc$, the kit would comprise a vial containing the chelate-HLE inhibitor conjugate together with a pharmaceutically acceptable reducing agent such as sodium dithionite, sodium bisulphite, ascorbic acid, formamidine sulphonic acid, stannous ion, Fe(II) or Cu(I), preferably a stannous salt such as stannous chloride or stannous tartrate. Alternatively, the chelating agent-HLE inhibitor conjugate could be present as a metal complex which, upon addition of the radiometal, undergoes transmetallation (i.e. ligand exchange) giving the desired product. The kit is preferably lyophilised and is designed to be reconstituted with sterile $^{99m}Tc$-pertechnetate ($TcO_4^-$) from a $^{99m}Tc$ radioisotope generator to give a solution suitable for human administration without further manipulation.

The agents of the present invention may also be provided in a unit dose form ready for human injection and could for example be supplied in a pre-filled sterile syringe. When the detectable moiety is a radioactive isotope such as $^{99m}Tc$, the syringe containing the unit dose would also be supplied within a syringe shield (to protect the operator from potential radioactive dose).

The above kits or pre-filled syringes may optionally contain further ingredients such as buffers; pharmaceutically acceptable solubilisers (e.g. cyclodextrins or surfactants such as Pluronic, Tween or phospholipids); pharmaceutically acceptable stabilisers/antioxidants (such as ascorbic acid, gentisic acid or para-aminobenzoic acid) or bulking agents for lyophilisation (such as sodium chloride or mannitol).

The structures of particular compounds 1–52 are set out below. Preparation of these compounds is described in Examples 1 to 12. NMR data for the compounds is given in Tables 1 to 19. Biological properties of compounds 4, 4a, 4b, 16, 17, 24, 28, 38, 42, 48, 49, 51 and 52 are shown in Examples 13 to 17 and in Tables 20 to 25.

COMPOUND STRUCTURES

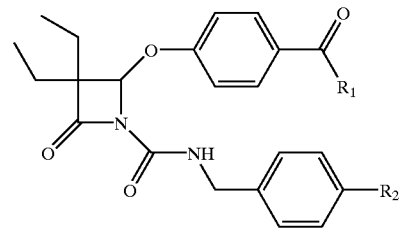

| Compound number | $R_1$ | $R_2$ |
|---|---|---|
| 2 | Ot-Bu | I |
| 3 | OH | I |
| 4 | 4-methyl-piperazinyl | I |
| 5 | 4-methyl-piperazinyl | $Sn(n-Bu)_3$ |

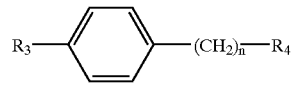

| Compound number | $R_3$ | $R_4$ | n |
|---|---|---|---|
| 1 | I | NCO | 1 |
| 6 | OH | NHBOC | 2 |
| 7 | OBn | NHBOC | 2 |
| 8 | OBn | $NH_2$ | 2 |
| 9 | OBn | NCO | 2 |

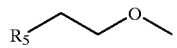

| Compound number | $R_5$ |
|---|---|
| 10 | TsO |
| 11 | $Ph_3CS$ |

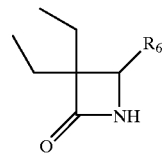

| Compound number | $R_6$ |
|---|---|
| 12 | $SCH_2CH_2OCH_3$ |

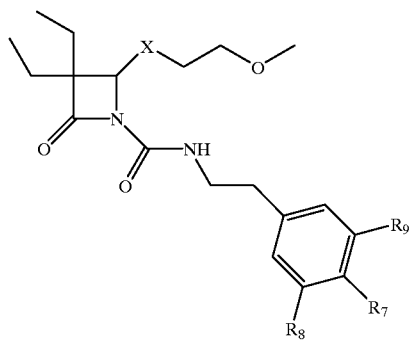

| Compound number | X | $R_7$ | $R_8$ | $R_9$ |
|---|---|---|---|---|

-continued

COMPOUND STRUCTURES

| | | | | |
|---|---|---|---|---|
| 13 | S | OBn | H | H |
| 14 | $SO_2$ | OBn | H | H |
| 15 | $SO_2$ | OH | H | H |
| 16 | $SO_2$ | OH | I | H |
| 17 | $SO_2$ | OH | I | I |

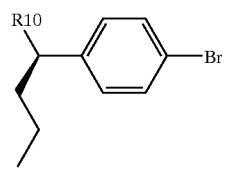

| Compound number | $R_{10}$ |
|---|---|
| 18 | COOH |
| 19 | CNO |

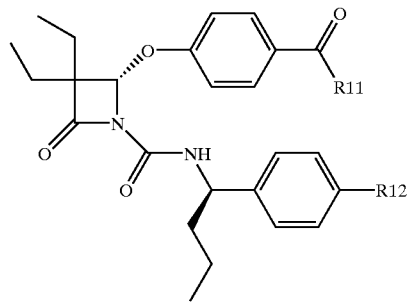

| Compound number | $R_{11}$ | $R_{12}$ |
|---|---|---|
| 20 | Ot-Bu | Br |
| 21 | OH | Br |
| 22 | 4-methylpiperazinyl | Br |
| 23 | 4-methylpiperazinyl | Sn(n-Bu)$_3$ |
| 24 | 4-methylpiperazinyl | I |

Compound 25

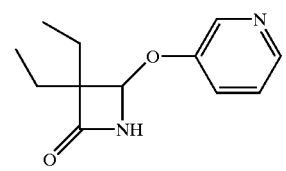

| Compound number | $R_{13}$ |
|---|---|
| 26 | Br |
| 27 | Sn(n-Bu)$_3$ |
| 28 | I |

-continued

COMPOUND STRUCTURES

| Compound number | $R_{14}$ | $R_{15}$ |
|---|---|---|
| 29 | COOH | NHCO$_2$t-Bu |
| 30 | CO$_2$CH$_2$Ar | NHCO$_2$t-Bu |
| 31 | CO$_2$CH$_2$Ar | NH$_3^+$Cl$^-$ |
| 35 | CO$_2$CH$_2$Ar | NCO |

| Compound number | $R_{16}$ |
|---|---|
| 32 | OCH$_2$Ar |
| 33 | OH |

Compound 34

| Compound number | $R_{17}$ |
|---|---|
| 36 | OCH$_2$Ar |
| 37 | OH |
| 38 | Ligand 1 |

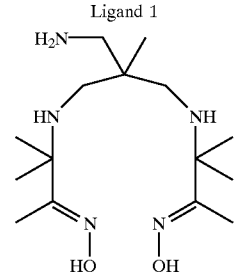

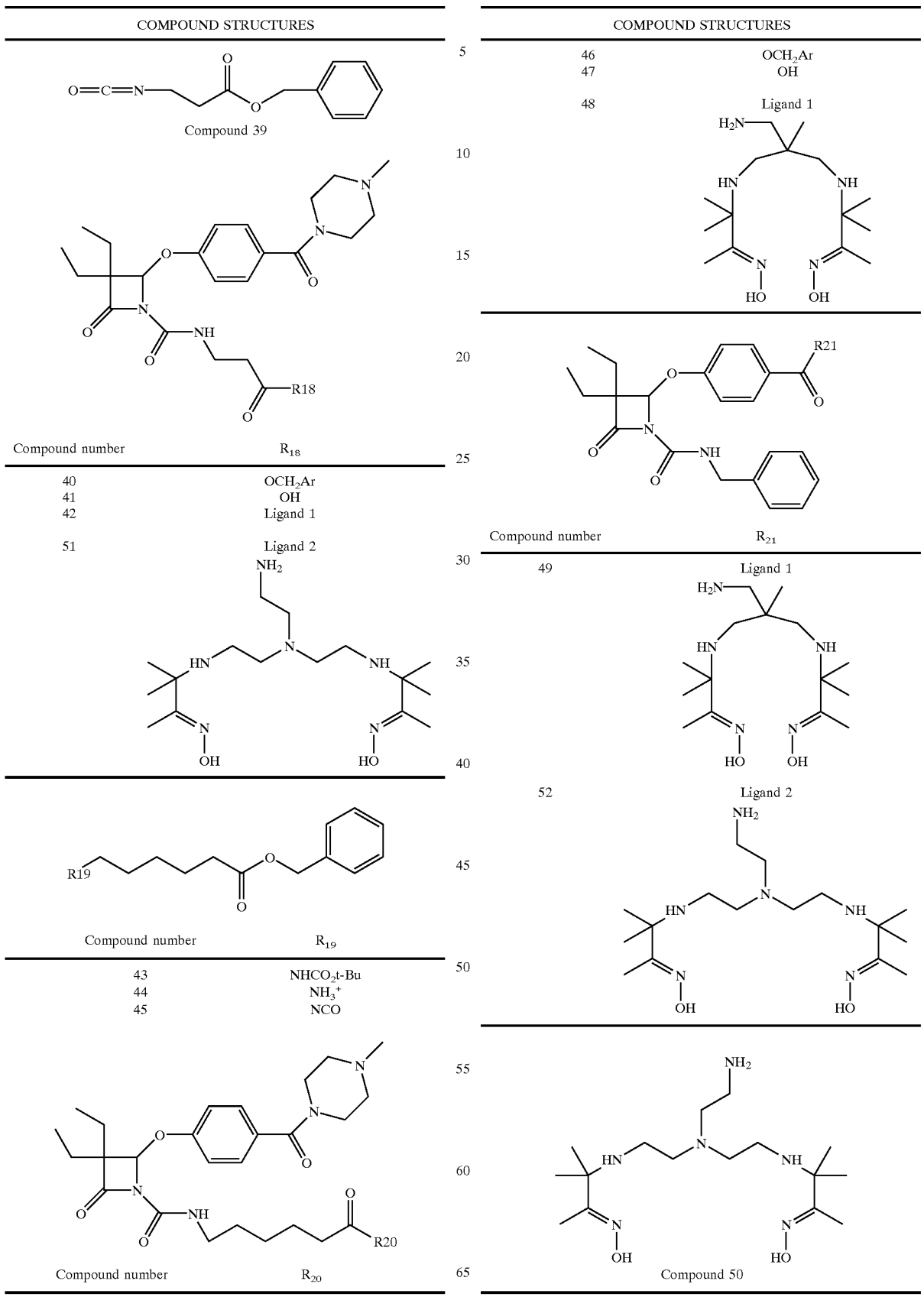

In one aspect of the present invention, the desired agent is required to label human granulocytes selectively in whole blood (either in vitro or in vivo). In normal human blood erythrocytes outnumber granulocytes by a factor of at least 1000:1 but erythrocytes do not accumulate at sites of infection/inflammation hence the labelled compound must exhibit high selectivity for granulocytes. Studies on the in vitro human blood cell uptake of $^{123}$I-labelled and $^{99m}$Tc-labelled β-lactam HLE inhibitors have demonstrated selective uptake in human granulocytes (see Example 14 and Table 23). Table 23 shows that compounds 4, 4a, 4b, 16, 17, 24, 28, 38, 42, 48, 49, 51 and 52 all show some degree of selectivity for granulocytes over a mixture of monocytes/lymphocytes when approximately equivalent numbers of monocytes/lymphocytes and granulocytes are present. Since human granulocytes contain significant levels of HLE whereas erythrocytes (red blood cells), monocytes and lymphocytes (subsets of the leucocyte cell population) contain essentially no HLE, this selectivity is a strong indication that affinity for HLE is involved. Furthermore, Table 23 shows that there is a correlation between the in vitro potency (measured for the non-radioactive iodine-labelled compounds and for the unlabelled chelate conjugates, compounds 38, 42, 48, 49, 51 and 52) and selectivity for granulocytes. The implication is that retention within the granulocyte is due to binding to intracellular elastase. Preferred synthetic HLE inhibitors of the present invention are therefore those with an in vitro potency ($k_{inact}/K_i$) of greater than 10,000 M/sec.

Whole blood also contains plasma proteins which are capable of binding to a wide range of substances and hence may compete effectively for the compound once it is introduced into the blood. Hence the preferred agent should also exhibit low plasma protein binding (PPB). Preferred compounds have a PPB of less than 95%. Most preferred have a PPB of less than 60%. Since lipophilic compounds are particularly susceptible to non-specific plasma protein binding, preferred compounds have an octanol/water partition coefficient (LogP) of ≦2. When intracellular HLE is the target and consequently the agent must be capable of crossing cell membranes, compounds with a minimum octanol/water partition coefficient (P) of 0.3 are preferred. Table 23 shows that, in human whole blood, compounds 4, 16 and 24 exhibit equivalent uptake in granulocytes and erythrocytes. This implies a selectivity factor for granulocytes over erythrocytes of at least 1000:1 and shows that the compounds of the present invention are capable of successfully labelling granulocytes in human whole blood despite the competition from excess erythrocytes and plasma proteins. It is believed that the superior granulocyte selectivity of compound 4 may be due to a combination of HLE potency and reduced non-specific binding to red blood cells or plasma proteins. It is postulated that the amine substituent facilitates selective retention in granulocytes due to diffusion of the uncharged inhibitor into the cell and its subsequent trapping via protonation of the basic piperazine amine within the more acidic milieu of the azurophil granule of the granulocyte. The protonated inhibitor cannot readily diffuse back across the granulocyte membrane. Such more acidic environments are not present within erythrocytes, monocytes or lymphocytes.

By virtue of the single substituent at the 4 position of the azetidinone ring, compound 4 has a chiral centre. The enantiomers were resolved (Example 1, step F) and one (4a) was found to exhibit markedly superior in vitro potency and granulocyte selectivity (Table 23) compared to the other (4b). Thus efficacy is highly sensitive to stereochemical effects, i.e. chirality. Therefore chiral compounds are also encompassed by the present invention.

Further improvements in potency have been achieved by the introduction of alkyl substituents at the homochiral benzylic $R_1$ position, demonstrated by compounds 24 and 28, since these are known to give more potent HLE inhibitors (EP 0595557 A1) e.g.:

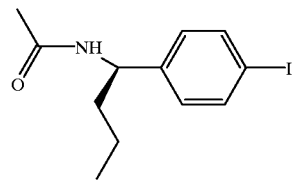

The radiolabelled β-lactam HLE inhibitors of the present invention have also been studied in vivo in a rat model of inflammation/infection. The results on such studies are given in Table 24. The known inflammation/infection agent $^{99m}$Tc-HMPAO ex-vivo labelled human leucocytes was shown to locate at the site of infection in the model used. $^{99m}$Tc-red blood cells was used as the negative control agent comparison. It can be seen that $^{123}$I-labelled compounds 4/4a show significantly better uptake in the infected region than the $^{99m}$Tc-rbc control, and have characteristics which more closely resemble the proven infection agent $^{99m}$Tc-wbc. When $^{123}$I-compound 4 is used to label human leucocytes ex-vivo the infected/normal ratio is higher than that obtained by direct injection. It is believed that the target to background ratios obtained in the rat model of infection/inflammation almost certainly underestimate the human situation because the potency of similar β-lactam inhibitors for rat elastase is known to be up to 2 orders of magnitude less than that for human leucocyte elastase.

Experiments with human plasma clots in vitro have been performed as described in Example 17. In clots enriched with granulocytes to a final concentration of $10^6$/ml there was an approximate 7–9 fold increase in the uptake of a potent elastase inhibitor compared to those clots formed without added cells. This observation indicates the potential for radiolabelled β-lactam HLE inhibitors to be specifically taken up in thrombi and other lesions where granulocyte accumulation is active.

Table 25 compares the thyroid uptake of the radioiodine compounds of the present invention with that of free $^{123}$I-iodide ion. The lack of thyroid uptake is evidence that the compounds do not undergo in vivo metabolic de-iodination. There was no evidence either for the release of pertechnetate in animals dosed with $^{99m}$Tc-labelled HLE inhibitors. This implies that the technetium is not released from the chelate conjugate in vivo.

| Abbreviations | |
|---|---|
| HLE = | human leucocyte elastase |
| PPB = | plasma protein binding |
| rbc = | red blood cell |
| wbc = | white blood cell |
| ACD = | acid citrate dextrose |
| HBSS = | Hanks balanced salt solution |
| RCP = | radiochemical purity |
| Me = | methyl |
| Et = | ethyl |
| $^t$Bu = | tertiary-butyl |
| Ph = | phenyl |

-continued

| Abbreviations | |
|---|---|
| Bn = | benzyl |
| Ac = | acetyl |
| Ts = | tosyl, i.e. para-toluenesulphonyl |
| Ar = | aryl |
| DMF = | N,N-dimethyl formamide |
| DMSO = | dimethyl sulphoxide |
| THF = | tetrahydrofuran |
| LDA = | lithium diisopropylamide |
| PAA = | peracetic acid |
| TFA = | trifluoroacetic acid |
| BOC = | tertiary-butoxycarbonyl |
| HBTU = | O-(1H-benzotriazol-1-yl)-N,N,N',N'-tetramethyluronium hexafluorophosphate |
| DMAP = | 4-(N,N-dimethylamino)pyridine |
| MCPBA = | meta-chloroperbenzoic acid |

EXPERIMENTAL

Example 1

4-[4-[[(4-Methyl)piperazin-1-yl]carbonyl]phenoxyl-1-[(4-iodo)benzylaminocarbonyl]-3,3-diethyl-2-azetidinone (compound 4)

Step A 4-Lodobenzylisocyanate (Compound 1)

To a solution of triphosgene (1.27 g, 4.28 mmol) in refluxing ethyl acetate (20 ml) under nitrogen was added dropwise, over 2 hours, a solution of 4-iodobenzylamine (1.0 g, 4.29 mmol) in dichloromethane (40 ml). The reaction mixture was heated at reflux for a further 3 hours, filtered whilst hot and the filtrate concentrated in vacuo to give the title compound (1.10 g, 99%) as a yellow oil.

Step B 4-[4-[(1,1-Dimethylethoxy)carbonyl]phenoxy]-1-[(4-iodo)benzylaminocarbonyl]-3,3-diethyl-2-azetidinone (Compound 2)

According to the method of Shrenik et al (J. Med. Chem., 35, 3745–3754 (1992)), 4-iodobenzylisocyanate (1.10 g, 4.25 mmol) and 4-[4-[(1,1-dimethylethoxy)carbonyl]phenoxy-3,3-diethyl-2-azetidinone (J. Med. Chem., 35, 3745–3754 (1992)) (0.62 g, 1.96 mmol) gave, following purification by flash column chromatography (gradient from petrol to EtOAc/petrol, 1:3), the title compound (0.72 g, 64%) as a solid.

Step C 4-[(4-Carboxy)phenoxy]-3,3-diethyl-1-[(4-iodo)benzylaminocarbonyl]-2-azetidinone (Compound 3)

According to the method of Shrenik et al (J. Med. Chem., 35, 3745–3754 (1992)), 4-[4-[(1,1-dimethylethoxy)carbonyl]phenoxy]-1-[(4-iodo)benzylaminocarbonyl]-3,3-diethyl-2-azetidinone (0.72 g, 1.2 mmol) gave, following recrystallisation (Et$_2$O/EtOAc), the title compound (0.44 g, 68%) as a solid.

Step D 4-[4-[[(4-Methyl)piperazin-1-yl]carbonyl]phenoxy]-1-[(4-iodo)benzylaminocarbonyl]-3,3-diethyl-2-azetidinone (Compound 4)

According to the method of Doherty et al (EP 0 595 557 A1), 4-[(4-carboxy)phenoxy]-3,3-diethyl-1-[(4-iodo)benzylaminocarbonyl]-2-azetidinone (0.44 g, 0.84 mmol) gave, following purification by flash column chromatography (gradient from EtOAc to MeOH/EtOAc, 1:4), the title compound (0.31 g, 79%) as a yellow oil.

Step E 4-[4-[[(4-Methyl)piperazin-1-yl]carbonyl]phenoxy]-1-[[4-tri-(n-butyl)stannyl]benzylaminocarbonyl]-3,3-diethyl-2-azetidinone (Compound 5)

4-[4-[[(4-Methyl)piperazin-1-yl]carbonyl]phenoxy]-1-[(4-iodo)benzylaminocarbonyl]-3,3-diethyl-2-azetidinone (0.02 g, 0.033 mmol) was dissolved in dry toluene (5 ml) under argon and heated to reflux. A catalytic amount of Pd(PPh$_3$)$_4$ (20 mg) and bis(tributyl)tin (100 ml, 0.198 mmol) were added and the resulting mixture heated at reflux for 5.5 hours. The reaction mixture was cooled to room temperature and filtered through a celite pad. The filtrate was concentrated in vacuo and the product purified by flash column chromatography (MeOH/Et$_3$N/EtOAc, 10:1:89) to give the title compound (5 mg, 20%).

Step F Resolution of the enantiomers of 4-[4-[[(4-Methyl)piperazin-1-yl]carbonyl]phenoxy]-1-[(4-iodo)benzylaminocarbonyl]-3,3-diethyl-2-azetidinone (Compound 4)

Compound 4 was separated into its two enantiomers, 4a and 4b, by chiral HPLC using HPLC system G, example 12 yielding isomer 4a from the fraction collected between 14 and 15 minutes and isomer 4b between 18 and 19 minutes. The solvents were removed in vacuo and each product extracted from the resulting residue into dichloromethane (4×20 ml), dried (MgSO$_4$) and concentrated in vacuo to give each enantiomer as a solid. Both products were reanalysed by chiral HPLC. The enantiomeric purities were shown to be greater than 75%.

Step G Synthesis of $^{123}$I-labelled 4-[4-[[(4-Methyl)piperazin-1-yl]carbonyl]phenoxy]-1-[(4-iodo)benzylaminocarbonyl]-3,3-diethyl-2-azetidinone (Compound 4) (Racemate)

4-[4-[[(4-Methyl)piperazin-1-yl]carbonyl]phenoxy]-1-[[4-tri-(n-butyl)stannyl]benzylaminocarbonyl]-3,3-diethyl-2-azetidinone in MeOH (50 μg, 0.6×10$^{-7}$ mol, 50 μl) was added to ammonium acetate buffer (pH 4, 0.2 M, 200 μl) in a 1 ml Eppendorf vial, followed by aqueous Na$^{127}$I in 0.01 M NaOH (7.5 μg, 0.5×10$^{-7}$ mol, 10 μl) and Na$^{123}$I (50 μl, carrier free, 50–100 MBq). The solution was thoroughly mixed and PM (0.01 M, ca. 1×10$^{-7}$ mole, 10 μl) added. The solution was again thoroughly mixed and incubated at ambient laboratory temperature for at least 5 minutes and the desired product HPLC purified using system B, example 12. The organic eluent component in the purified sample was removed and the sample diluted with sodium phosphate buffer (pH 7.4, volume variable) to ensure the purified compound was present in a biologically acceptable medium for testing. The radiochemical purity of the purified compound 4 (racemate) was measured using HPLC system B, example 12 before and after in vitro or in vivo testing. Results of RCP measurement are presented in Table 20. The identity of the $^{123}$I species was confirmed by HPLC co-elution with the chemically characterised $^{127}$I analogue (Example 1, step D). The retention times of the $^{123}$I and $^{127}$I species are presented in Table 21.

Step H Synthesis of $^{123}$I Labelled Compounds 4a and 4b

A sample of $^{123}$I-compound 4 racemate was synthesised and purified according to the HPLC method detailed in system C, example 12. This was to ensure that the pH of the purified racemic compound was compatible with the HPLC column material used for purification of optical isomers (below). The organic HPLC eluent was removed in vacuo at ambient laboratory temperature and the sample then diluted with sodium phosphate buffer (pH 6.0) to make the total volume ca 1 ml. The racemate was purified into the two optical isomers using the HPLC system D, example 12. The two enantiomers, 4a and 4b, were collected and the is HPLC organic eluent removed in vacuo and the radiochemical (chiral) purity measured after testing using HPLC system D, Example 12. Results of RCP testing are presented in Table 20.

Example 2

4-[2-Methoxyethylsulfonyl]-1-[(4-hydroxy) (3-iodo) phenylethylaminocarbonyl]-3,3-diethyl-2-azetidinone (Compound 16) and 4-[2-Methoxyethylsulfonyl]-1-[(3,5-diiodo) (4-hydroxy) phenylethylaminocarbonyl]-3.3-diethyl-2-azetidinone (Compound 17)

Step A N-t-Butoxycarbonyl (4-Hydroxy)-2-phenylethylamine (Compound 6)

Tyramine (0.20 g, 1.46 mmol) was dissolved in methanol (5 ml) at room temperature under nitrogen. A solution of di-tert-butyldicarbonate (0.318 g, 1.46 mmol) in methanol (1 ml) was added followed by triethylamine (200 ml, 1.46 mmol). The reaction mixture was stirred for 4.5 hours and the solvent then removed in vacuo. The residue was partitioned between ethyl acetate and water. The organic layer was separated, dried ($Na_2SO_4$) and concentrated in vacuo to give the crude product. Purification by flash column chromatography (petrol/EtOAc, 1:1) gave the title compound (0.34 g, 98%) as a yellow oil.

Step B N-t-Butoxycarbonyl (4-Benzyloxy)-2-phenylethylamine (Compound 7)

Sodium hydride (0.046 g, 1.14 mmol) was suspended in dry THF (5 ml) at room temperature under nitrogen. A solution of N-t-butoxycarbonyl (4-hydroxy)-2-phenylethylamine (0.27 g, 1.14 mmol) in dry THF (5 ml) was added dropwise to the reaction mixture over 20 minutes. Benzyl bromide (135 μl, 1.14 mmol) was added as a single aliquot and the resulting mixture stirred for 24 hours. The reaction was quenched by pouring into water (50 ml) and the aqueous layer extracted with diethyl ether (3×20 ml). The combined organic extracts were dried ($MgSO_4$) and concentrated in vacuo. The crude product was purified by flash column chromatography (petrol/$Et_2O$, 8:1) to give the title compound (0.217 g, 58%) as a solid.

Step C (4-Benzyloxy)-2-phenylethylamine hydrochloride salt (Compound 8)

N-t-Butoxycarbonyl (4-benzyloxy)-2-phenylethylamine (0.199 g, 0.608 mmol) was dissolved in a 3 M solution of hydrochloric acid in ethyl acetate (10 ml) and the mixture stirred for 1 hour at room temperature. The precipitate was isolated by filtration to give a white solid (0.056 g) and the filtrate concentrated in vacuo to obtain a pale yellow solid (0.079 g). Both products were combined to give a total sample of the title compound (0. 135 g, 84%) as a pale yellow solid.

Step D (4-Benzyloxy)-2-phenylethylisocyanate (Compound 9)

(4-Benzyloxy)-2-phenylethyiamine hydrochloride salt (1.413 g, 5.35 mmol) was taken up in ethyl acetate (15 ml) and 2M aqueous sodium hydroxide (3 ml) and the resulting mixture stirred at room temperature for 1 hour. The aqueous layer was separated and extracted with dichloromethane (3×20 ml). The organic extracts were combined and concentrated in vacuo to obtain the free amine (1.32 g, 97%). According to the procedure given in example 1, step A, a portion of this amine (0.19 g, 0.84 mmol) gave the title compound (0.187 g, 88%) as a solid.

Step E Ethylene Glycol Methyl Ether Tosylate (Compound 10)

To tosyl chloride (50.0 g, 0.263 mol) at 0° C. and under nitrogen were added anhydrous dichloromethane (80 ml), anhydrous pyridine (23 ml, 24.3 g, 0.29 mol), 2-methoxyethanol (21.0 ml, 20.0 g, 0.263 mol) and a catalytic quantity of DMAP. After 10 minutes the mixture was warmed to room temperature, at which it was stirred for 16 hours. Dichloromethane (100 ml) and 1 M aqueous hydrochloric acid (50 ml) were added. The organic layer was isolated and washed with 1 M aqueous hydrochloric acid (4×30 ml) and water (4×30 ml), dried ($Na_2SO_4$) and concentrated in vacuo to give the title compound (51.68 g, 85%) as an oil.

Step F S-Triphenylmethyl 2-Methoxyethanethiol (Compound 11)

To sodium hydride (2.17 g, 0.09 mol) under nitrogen was added anhydrous THF (50 ml). The mixture was cooled to 0° C. and triphenylmethylmercaptan (24.88 g, 0.09 mol) in anhydrous THF (50 ml) added dropwise over 15 minutes. After a further 10 minutes at 0° C. the mixture was warmed to room temperature, at which it was stirred for 1 hour. The mixture was then recooled to 0° C. and ethylene glycol methyl ether tosylate (20.72 g, 0.09 mol) in dry THF (50 ml) added dropwise over 15 minutes. After warming to room temperature the mixture was left to stir for 16 hours. The mixture was filtered and the precipitate washed with dichloromethane. The combined filtrates were concentrated in vacuo. The residue was dissolved in dichloromethane, washed with water (3×50 ml), dried ($Na_2SO_4$) and concentrated in vacuo. Purification by flash column chromatography (gradient from 100% petrol to 100% EtOAc) and recrystallisation (petrol) gave the title compound (12.39 g, 41%) as a pale brown solid.

Step G 4-[2-Methoxyethylthio]-3,3-diethyl-2-azetidinone (Compound 12)

To S-triphenylmethyl 2-methoxyethanethiol (1.37 g, 4.1 mmol) in dichloromethane (30 ml) under nitrogen were added triethylsilane (0.953 g, 1.31 ml, 8.2 mmol) and trifluoroacetic acid (0.632 ml, 0.935 g, 8.2 mmol). The mixture was stirred at room temperature for 16 hours. Acetone (50 ml) was added and the mixture neutralised with 2 M aqueous sodium hydroxide. 1 M Aqueous sodium hydroxide (24 ml, 24 mmol), 4-acetoxy-3,3-diethyl-2-azetidinone (J. Med. Chem., 35, 3745–3754 (1992)) (0.690 g, 6.00 mmol) and acetone (10 ml) were then added and the mixture stirred at room temperature for 23 hours. The solvents were removed in vacuo and to the residue were added water (50 ml) and dichloromethane (50 ml). The organic layer was isolated and the water layer extracted further with dichloromethane (3×30 ml). The 4 organic layers were combined and washed with water (30 ml) and saturated brine (30 ml), dried ($Na_2SO_4$) and concentrated in vacuo. Purification by flash column chromatography (gradient from petrol/EtOAc, 9:1 to EtOAc) gave the title compound (0.51 g, 63%) as an oil.

Step H 4-[2-Methoxyethylthio]-1-[(4-benzyloxy) phenylethylaminocarbonyl]-3,3-diethyl-2-azetidinone (Compound 13)

According to the method of Shrenik et al (J. Med. Chem., 35, 3745–3754 (1992)) 4-[2-methoxyethylthio]-3,3-diethyl-2-azetidinone (550 mg, 2.53 mmol) and (4-benzyloxy)-2-phenylethylisocyanate, prepared as in example 2, step D, (1.366 g, 5.39 mmol) gave, following purification by flash column chromatography (EtOAc/petrol, 7:3), the title compound (391 mg, 33%) as an oil.

Step I 4-[2-Methoxyethylsulfonyl]-1-(4-benzyloxy) phenylethylaminocarbonyl]-3,3-diethyl-2-azetidinone (Compound 14)

To 4-[2-methoxyethylthio]-1-[(4-benzyloxy) phenylethylaminocarbonyl]-3,3-diethyl-2-azetidinone (358 mg, 0.76 mmol) in dichloromethane (10 ml) was added excess metachloroperoxybenzoic acid (MCPBA) (approximately 50% pure, 525 mg) and the mixture stirred at room temperature for 16 hours. The mixture was poured into an aqueous solution containing 8% (w/v) sodium bicarbonate and 8% (w/v) sodium sulphite (50 ml) and stirred vigorously at room temperature for 30 minutes. The organic layer was isolated and washed with saturated brine (5 ml) and water (5 ml). The aqueous layer was extracted with dichloromethane (20 ml). The organic layers were combined, dried ($Na_2SO_4$) and concentrated in vacuo. Purification by flash column chromatography (petrol/EtOAc, 7:3) gave the title compound (314 mg, 82%) as an oil.

Step J 4-[2-Methoxyethylsulfonyl]-1-(4-hydroxy) phenylethylaminocarbonyl]-3,3-diethyl-2-azetidinone (Compound 15)

Cyclohexene (400 µl, 3.95 mmol) was added to a solution of 4-[2-methoxyethylsulfonyl]-1-[4-benzyloxy) phenylethylaminocarbonyl]-3,3-diethyl-2-azetidinone (195 mg, 0.39 mmol) in dry ethanol (7 ml) at room temperature under argon. 10% Palladium on charcoal (202 mg) was added and the reaction mixture heated at reflux for 4 hours. The reaction mixture was then allowed to cool to room temperature, filtered through a pad of celite, washing with ethanol (15 ml), and the filtrate concentrated in vacuo. The crude product was purified by flash column chromatography (petrol/EtOAc, 1:1) to give the title compound (127 mg, 79%) as an oil.

Step K 4-[2-Methoxyethylsulfonyl]-1-[(4-hydroxy)(3-iodo) phenylethylaminocarbonyl]-3,3-diethyl-2-azetidinone (Compound 16)

To 4-[2-methoxyethylsulfonyl]-1-[(4-hydroxy) phenylethylaminocarbonyl]-3,3-diethyl-2-azetidinone (52 mg, $1.3 \times 10^{-4}$ mol) dissolved in MeOH (10 ml) was added NaI (19 mg, $1.3 \times 10^{-4}$ mol), and aqueous PAA (0.1 M, $1.3 \times 10^{-4}$ mol, 1.27 ml). The solution was stirred at ambient laboratory temperature and further mole equivalents of PAA were added at approximately 1 and 2 hours after the addition of the first aliquot of PAA. The dissolved product was HPLC purified using system E, Example 12. The purified HPLC fractions were concentrated in vacuo to give the title compound (21 mg, 30%).

Step L 4-(2-Methoxyethylsulfonyl)-1-[(3,5-diiodo)(4-hydroxy)phenylethylaminocarbonyl]-3,3-diethyl-2-azetidinone (Compound 17)

To 4-[2-methoxyethylsulfonyl]-1-[(4-hydroxy) phenylethylaminocarbonyl]-3,3-diethyl-2-azetidinone (13 mg, $3.1 \times 10^{-5}$ mol) was added NaI (5 mg, $3.1 \times 10^{-5}$ mol) and aqueous PAA (0.3 ml, 0.1 M, $3.1 \times 10^{-5}$ mol). The solution became orange/brown immediately on addition of peracetic acid and was stirred at ambient laboratory temperature. Further aliquots of NaI ($3.1 \times 10^{-5}$ mol) and PAA (0.3 ml, $3.1 \times 10^{-5}$ mol) were added at approximately 2½ hours and 4 hours post reaction initiation. The dissolved product was HPLC purified using system E, Example 12. The purified fractions were concentrated in vacuo to give the title compound (4.4 mg, 21%).

Step M Synthesis of $^{123}$I-labelled 4-[2-Methoxyethylsulfonyl]-1-[(4-hydroxy)(3-iodo) phenylethylaminocarbonyl]-3,3-diethyl-2-azetidinone (Compound 16)

4-[2-Methoxyethylsulfonyl]-1-[(4-hydroxy) phenylethylaminocarbonyl]-3,3-diethyl-2-azetidinone in MeOH (50 µg, $1 \times 10^{-7}$ mol, 50 µl) was iodinated according to the procedure described in Example 1, step G. The product was purified by HPLC using system A, Example 12 and diluted with sodium phosphate buffer (pH 7.4) in an identical manner to that detailed in Example 1, step G. RCP measurements are detailed in Table 20. The identity of the $^{123}$I species was confirmed by HPLC co-elution with the chemical characterised $^{127}$I analogue (Example 2, step K). The retention times of the $^{123}$I and $^{127}$I species are presented in Table 21.

Step N Synthesis of $^{123}$I-labelled 4-(2-Methoxyethylsulfonyl)-1-[(3,5-diiodo)(4-hydroxy) phenylethylaminocarbonyl]-3,3-diethyl-2-azetidinone (Compound 17)

The synthesis of the title compound was identical to the method used in example 1, step G. This method produces a mixture (roughly 50:50) of mono-iodo and di-iodo species. The desired product was purified by HPLC using system A, Example 12, the organic eluent removed and the sample diluted with aqueous sodium phosphate buffer prior to testing as detailed in example 1, step G. The radiochemical purity of the purified compound was measured before and after screening using HPLC system A, Example 12. Results of RCP measurement are detailed in Table 20. The identity of the $^{123}$I-species was confirmed by HPLC coelution with the chemically characterised $^{127}$I analogue (Example 2, step L). The retention times of the $^{123}$I and $^{127}$I species are presented in Table 21.

Example 3

4S-[4-[[(4-Methyl)piperazin-1-yl]carbonyl] phenoxy]-1-[(R-α-n-propyl)-(4-iodo) benzyiaminocarbonyl]-3,3-diethyl-2-azetidinone (Compound 24)

Step A R-α-n-Propyl-(4-bromo)phenylacetic Acid (Compound 18)

According to the method of Finke et al (UK Patent Application GB 2 280 673 A), 4-bromophenylacetic acid (17.24 g, 0.08 mol) and 1-bromopropane (14.5 ml, 0.16 mol) gave, following purification by flash column chromatography (gradient petrol/acetic acid, 99:1 to petrol/EtOAc/acetic acid, 64:33:1), α-n-propyl-(4-bromo)phenylacetic acid (15.49 g, 75%). To the racemic acid was added R-(+)-α-methylbenzylamine and the resulting salt recrystallised three times from ethyl acetate. The salt was taken up in 2M aqueous HCl (100 ml) and extracted into dichloromethane (100 ml). The organic layer was dried ($Na_2SO_4$) and concentrated in vacuo to give the title compound (3.72 g) as an oil.

Step B R-α-n-Propyl-(4-bromo)phenylmethylisocyanate (Compound 19)

According to the method of Finke et al (UK Patent Application GB 2 280 673), R-α-n-propyl-(4-bromo) phenylacetic acid (2.00 g, 7.78 mmol) gave the title compound (1.90 g, 96%) as an oil.

Step C 4S-[4-[(1,1-Dimethylethoxy)carbonyl]phenoxy]-1-[(R-α-n-propyl)-(4-bromo)benzylaminocarbonyl]-3, 3-diethyl-2-azetidinone (Compound 20)

According to the method of Shrenik et al (J. Med. Chem., 35, 3745–3754 (1992)), R-α-n-propyl-(4-bromo) phenylmethyl isocyanate (1.9 g, 7.48 mmol) and 4-[4-[(1, 1-dimethylethoxy)carbonyl]phenoxy]-3,3-diethyl-2-azetidinone (J. Med. Chem., 35, 3745–3754 (1992)) (1.28 g, 4.0 mmol) gave, following purification by flash column chromatography (gradient from 100% petrol to petrol/ EtOAc, 1:1), the title compound (0.73 g, 32%) as an oil.

Step D 4S-[(4-Carboxy)phenoxy]-1-[(R-α-n-propyl)-(4-bromo)benzylaminocarbonyl]-3,3-diethyl-2-azetidinone (Compound 21)

According to the method of Shrenik et al (J. Med. Chem., 35, 3745–3754 (1992)), 4S-[4-[(1,1-dimethylethoxy) carbonyl]phenoxy]-1-[(R-α-n-propyl)-(4-bromo) benzylaminocarbonyl]-3,3-diethyl-2-azetidinone (0.73 g, 1.27 mmol) gave the title compound (0.66 g, 100%) as a solid.

Step E 4S-[4-[[(4-Methyl)piperazin-1-yl]carbonyl] phenoxy]-1-[(R-α-n-propyl)-(4-bromo)

benzylaminocarbonyl]-3,3-diethyl-2-azetidinone (Compound 22)

According to the method of Doherty et al (EP 0 595 557 A1), 4S-[(4-carboxy)phenoxy]-1-[(R-α-n-propyl)-(4-bromo)benzylaminocarbonyl]-3,3-diethyl-2-azetidinone (0.66 g, 1.27 mmol) gave, following purification by flash column chromatography (gradient from hexane to EtOAc/hexane, 1:1 to MeOH/EtOAc, 1:9) and recrystallisation (diethyl ether/petrol), the title compound (0.37 g, 60%) as white crystals.

Step F 4S-[4-[[(4-Methyl)piperazin-1-yl]carbonyl] phenoxy]-1-[(R-α-n-propyl]-[4-[tri-(n-butyl)-stannyl] benzylaminocarbonyl]-3,3-diethyl-2-azetidinone (Compound 23)

According to the procedure described in Example 1, step E, 4S-[4-[[(4-methyl)piperazin-1-yl]carbonyl]phenoxy]-1-[(R-α-n-propyl)-(4-bromo)benzylaminocarbonyl]-3,3-diethyl-2-azetidinone (80 mg, 0.13 mmol) gave, following purification by HPLC using system J, Example 12, the title compound (15.5 mg, 15%) as an oil.

Step G Synthesis of $^{123}$I-labelled 4S-[4-[[(4-methyl) piperazin-1-yl]carbonyl]phenoxy]-1-[(R-α-n-propyl)-(4-iodo)benzylaminocarbonyl]-3,3-diethyl-2-azetidinone (Compound 24)

According to the procedure described in Example 1, step G, 4S-[4-[[(4-methyl)piperazin-1-yl]carbonyl]phenoxy]-1-[(R-α-n-propyl)-[4-[tri-(n-butyl)-stannyl] benzylaminocarbonyl]-3,3-diethyl-2-azetidinone (50 μg, 6.18×10$^{-8}$ mol) gave the title compound.

Example 4

4S-(Pyridyl-3-oxy)-1-[(R-α-n-propyl)-(4-iodo) benzylaminocarbonyl]-3,3-diethyl-2-azetidinone (Compound 28)

Step A 4-(Pyridyl-3-oxy)-3,3-diethyl-2-azetidinone (Compound 25)

According to the method of Shrenik et al (J. Med. Chem., 35, 3745–3754 (1992), 3-hydroxypyridine (0.598 g, 6.291 mol) and 4-acetoxy-3,3-diethyl-2-azetidinone (J. Med. Chem., 35, 3745–3754 (1992)) (1.00 g, 5.40 mol) gave, following purification by flash column chromatography (MeOH/EtOAc, 1:4), the title compound (900 mg, 76%) as an oil.

Step B 4S-(Pyridyl-3-oxy)-1-[(R-α-n-propyl)-(4-bromo) benzylaminocarbonyl]-3,3-diethyl-2-azetidinone (Compound 26)

According to the method of Shrenik et al (J. Med. Chem., 35, 3745–3754 (1992)), R-α-n-propyl-(4-bromo) phenylmethyl isocyanate, prepared as in example 3, step B (1.32 g, 5.19 mmol) and 4-(pyridyl-3-oxy)-3,3-diethyl-2-azetidinone (0.573 mg, 2.60 mmol) gave, following purification by flash column chromatography (gradient from diethyl ether/petrol, 1:1 to diethyl etherlpetrol, 7:1 to diethyl etherlpetrol, 9:1), the title compound (0.35 g, 28%) as an oil.

Step C 4S-(Pyridyl-3-oxy)-1-[(R-α-n-propyl)-[[4-tri-(n-butyl)-stannyl]benzylaminocarbonyl]-3,3-diethyl-2-azetidinone (compound 27)

According to the procedure described in Example 1, step E, 4S-(pyridyl-3-oxy)-1-[(R-α-n-propyl)-(4-bromo) benzylaminocarbonyl]-3,3-diethyl-2-azetidinone (90 mg, 0.19 mmol) gave, following purification by flash column chromatography (gradient from EtOAc/petrol, 1:4 to EtOAc/petrol, 1:1 to EtOAc/petrol, 7:3), the title compound (29 mg, 22%) as an oil.

Step D Synthesis of $^{123}$I-labelled 4S-(pyrdyl-3-oxy)-1-[(R-α-n-propyl)-(4-iodo)benzylaminocarbonyl]-3,3-diethyl-2-azetidinone (Compound 28)

According to the procedure described in Example 1, step G, 4S-(pyridyl-3-oxy)-1-[(R-α-n-propyl)-[[4-tri-(n-butyl)-stannyl]benzylaminocarbonyl]-3,3-diethyl-2-azetidinone (50 μg, 7.31×10$^{-8}$ mol) gave the title compound.

Example 5

Conjugate Between Chelate, 3,3,6,9,9-Pentamethyl-6-aminomethyl-4,8-diazaundecane-2,10-dionedioxime and 4-[4-[[(4-methyl)piperazin-1-yl] carbonyl]phenoxy]-1-[(4-carboxy) benzylaminocarbonyl]-3,3-diethyl-2-azetidinone (Compound 38)

Step A 4-(N-Boc-aminomethyl)benzoic Acid (Compound 29)

To a solution of 4-(aminomethyl)benzoic acid (1 g, 6.62 mmol) in 4M NaOH (21 ml) at room temperature was added di-tert-butyldicarbonate (1.67 ml, 7.28 mmol) and the mixture stirred for 19 hours. The reaction was acidified to pH 2.0 with concentrated hydrochloric acid and the mixture extracted with ethyl acetate (3×50 ml). The combined organic extracts were dried (Na$_2$SO$_4$) and concentrated in vacuo to give the title compound (1.136 g, 68%) as a solid.

Step B 4-(N-Boc-aminomethyi)benzoic Acid, Benzyl Ester (Compound 30)

To a mixture of 4-(N-Boc-aminomethyl)benzoic acid (500 mg, 1.99 mmol), DMAP (catalytic amount), benzyl alcohol (226 μl, 2.19 mmol) and dichloromethane (20 ml) was added dicyclohexylcarbodiimide (1M solution in dichloromethane, 2.19 ml, 2.19 mmol) and the mixture stirred at room temperature for 60 hours. The precipitate was removed by filtration and the filtrate concentrated in vacuo. Diethyl ether (50 ml) was added to the residue, the resulting precipitate removed by filtration and the filtrate concentrated in vacuo. Purification by flash column chromatography (petrol/EtOAc, 3:1) gave the title compound (412 mg, 61%) as a solid.

Step C 4-(Aminomethyl)benzoic Acid, Benzyl Ester, Hydrochloride Salt (Compound 31)

According to the procedure described in example 2, step C, 4-(N-Boc-aminomethyl)benzoic acid, benzyl ester (398 mg, 1.17 mmol) gave the title compound (288 mg, 93%) as a solid.

Step D 4-Benzyloxy-(1-N-methylpiperazine)benzamide (Compound 32)

According to the method of Doherty et al (EP 0 595 557 A1), benzyloxybenzoic acid (15.22 g, 0.06 mol) gave the title compound (18.93 g, 99%) as a pale yellow solid.

Step E 4-Hydroxy-(1-N-methylpiperazine)benzamide (Compound 33)

According to the procedure described in Example 2, step J, 4-benzyloxy-(1-N-methylpiperazine)benzamide (4.555 g, 0.015 mol) gave, following purification by flash column chromatography (MeOH/EtOAc, 1:9), the title compound (2.41 g, 73%) as a solid.

Step F 4-[4-[[(4-Methyl)piperazin-1-yl]carbonyl]phenoxy]-3,3-diethyl-2-azetidinone (Compound 34)

According to the method of Shrenik et al (J. Med. Chem., 35, 3745–3754 (1992)), 4-hydroxy-(1-N-methylpiperazine) benzamide (2.41 g, 0.011 mol) and 4-acetoxy-3,3-diethyl-2-azetidinone (J. Med. Chem., 35, 3745–3754 (1992), 3.04 g, 0.017 mol), followed by a further addition after 60 hours of 4-acetoxy-3,3-diethyl-2-azetidinone (0.95 g, 5.31 mmol) gave, following purification by flash column chromatography (gradient from petrol/EtOAc, 1:1 to MeOH/EtOAc, 1:9 to MeOH/EtOAc, 9:1), the title compound (1.60 g, 42%) as an oil.

Step G 4-(Benzyloxycarbonyl)benzylisocyanate (Compound 35)

To 4-(aminomethyl)benzoic acid, benzyl ester, hydrochloride salt, prepared as in Example 5, step C (288 mg, 1.04 mmol) at 0° C. was added saturated aqueous NaHCO$_3$ (15 ml) and dichloromethane (20 ml). After 20 minutes stirring was ceased and the two layers were allowed to separate. Phosgene (20% solution in toluene, 1.1 ml, 2.18 mmol) was added rapidly to the lower layer and stirring resumed immediately. After 1 hour the organic layer was isolated. The aqueous layer was extracted with dichloromethane (3×20 ml). The four organic layers were combined, dried (Na$_2$SO$_4$) and concentrated in vacuo to give the title compound (261 mg, 94%) as an oil.

Step H 4-[4-[[(4-Methyl)piperazin-1-yl]carbonyl]phenoxy]-1-[4-(benzyloxycarbonyl)benzylaminocarbonyl]-3,3-diethyl-2-azetidinone (Compound 36)

According to the method of Shrenik et al (J. Med. Chem., 35, 3745–3754 (1992)), 4-[4-[[(4-methyl)piperazin-1-yl]carbonyl]phenoxy]-3,3-diethyl-2-azetidinone (160 mg, 0.463 mmol) and 4-(benzyloxycarbonyl)benzylisocyanate (261 mg, 0.98 mmol) gave, following purification by flash column chromatography (MeOH/EtOAc, 1:4), the title compound (171 mg, 60%) as an oil.

Step I 4-[4-[[(4-Methyl)piperazin-1-yl]carbonyl]phenoxy]-1-[(4-carboxy)benzylaminocarbonyl]-3,3-diethyl-2-azetidinone (Compound 37)

According to the procedure described in Example 2, step J, 4-[4-[[(4-methyl)piperazin-1-yl]carbonyl]phenoxy]-1-[4-(benzyloxycarbonyl)benzylaminocarbonyl]-3,3-diethyl-2-azetidinone (159 mg, 0.26 mmol) gave the title compound (107 mg, 79%) as a solid.

Step J Conjugate Between Chelate, 3,3,6,9,9-Pentamethyl-6-aminomethyl-4,8-diazaundecane-2,10-dionedioxime and 4-[4-[[(4-Methyl)piperazin-1-yl]carbonyl]phenoxy]-1-[(4-carboxy)benzylaminocarbonyl]-3,3-diethyl-2-azetidinone (Compound 38)

To 4-[4-[[(4-methyl)piperazin-1-yl]carbonyl]phenoxy]-1-[(4-carboxy)benzylaminocarbonyl]-3,3-diethyl-2-azetidinone (30 mg, 0.057 mmol), DMAP (catalytic amount) and N-hydroxysuccinimide (7 mg, 0.063 mmol) in a mixture of dichloromethane (1 ml) and acetonitrile (1 ml) was added dicyclohexylcarbodiimide (1M solution in dichloromethane, 0.63 ml, 0.063 mmol) and the mixture stirred at room temperature under nitrogen for 19 hours. A solution of 3,3,6,9,9-pentamethyl-6-aminomethyl-4,8-diazaundecane-2,10-dionedioxime (WO 95/19187, 27 mg, 0.086 mmol) in acetonitrile (1 ml) was added and the mixture stirred for a further 5 hours. The mixture was filtered, diluted with acetonitrile (1 ml) and purified by HPLC using system H, Example 12 to give the title compound (2 mg, 4%) as a solid

Example 6

Conjugate Between Chelate, 3,3,6,9,9-Pentamethyl-6-aminomethyl-4,8-diazaundecane-2,10-dionedioxime and 4-[4-[[(4-methyl)piperazin-1-yl]carbonyl]phenoxy]-1-[(2-carboxy)ethylaminocarbonyl]-3,3-diethyl-2-azetidinone (Compound 42)

Step A 2-(Benzyloxycarbonyl)ethylisocyanate (Compound 39)

According to the procedure described in Example 5, step G, β-alanine benzylester-p-toluene sulphonate (3 g, 8.53 mmol) gave the title compound (1.44 g, 94%) as a liquid.

Step B 4-[4-[[(4-Methyl)piperazin-1-yl]carbonyl]phenoxy]-1-[2-(benzyloxycarbonyl)ethylaminocarbonyl]-3,3-diethyl-2-azetidinone (Compound 40)

According to the method of Shrenik et al (J. Med. Chem., 35, 3745–3754 (1992)), 4-[4-[[(4-methyl)piperazin-1-yl]carbonyl]phenoxy]-3,3-diethyl-2-azetidinone, prepared as in Example 5, step F, (0.68 g, 1.97 mmol) and 2-(benzyloxycarbonyl)ethylisocyanate (0.705 g, 3.94 mmol) gave, following purification by flash column chromatography (gradient from petrol/EtOAc, 1:1 to MeOH/EtOAc, 1:9 to MeOH/EtOAc, 1:1), the title compound (840 mg, 78%) as an oil.

Step C 4-[4-[[(4-Methyl)piperazin-1-yl]carbonyl]phenoxy]-1-[(2-carboxy)ethylaminocarbonyl]-3,3-diethyl-2-azetidinone (Compound 41)

According to the procedure described in Example 2, step J, 4-[4-[[(4-methyl)piperazin-1-yl]carbonyl]phenoxy]-1-[2-(benzyloxycarbonyl)ethylaminocarbonyl]-3,3-diethyl-2-azetidinone (420 mg, 0.76 mmol) gave the title compound (280 mg, 80%) as a solid.

Step D Conjugate Between Chelate, 3,3,6,9,9-pentamethyl-6-aminomethyl-4,8-diazaundecane-2,10-dionedioxime and 4-[4-[[(4-Methyl)piperazin-1-yl]carbonyl]phenoxy]-1-[(2-carboxy)ethylaminocarbonyl]-3,3-diethyl-2-azetidinone (Compound 42)

According to the procedure described in Example 5, step J, 4-[4-[[(4-methyl)piperazin-1-yl]carbonyl]phenoxy]-1-[(2-carboxy)ethylaminocarbonyl]-3,3-diethyl-2-azetidinone (100 mg, 0.22 mmol) and 3,3,6,9,9-pentamethyl-6-aminomethyl-4,8-diazaundecane-2,10-dionedioxime (WO 95/19187, 82 mg. 0.26 mmol) gave, following purification by HPLC using system H, Example 12, the title compound (4 mg, 3%) as an oil.

Example 7

Conjugate Between Chelate, 3,3,6,9,9-pentamethyl-6-aminomethyl-4,8-diazaundecane-2,10-dionedioxime and 4-[4-[[(4-methyl)piperazin-1-yl]carbonyl]phenoxy]-1-[(5-carboxy)pentylaminocarbonyl]-3,3-diethyl-2-azetidinone (Compound 48)

Step A N-Boc-aminocaproic Acid, Benzyl Ester (Compound 43)

According to the procedure described in Example 5, step B, N-Boc aminocaproic acid (1.0 g, 4.32 mmol) gave, following purification by flash column chromatography (petrol/EtOAc, 4:1), the title compound (1.34 g, 96%) as a liquid.

Step B Aminocaproic Acid, Benzyl Ester (Compound 44)

To N-Boc-aminocaproic acid, benzyl ester (1.125 g, 3.50 mmol) in dichloromethane (4 ml) was added trifluoroacetic acid (8 ml) and the mixture stirred at room temperature for 10 minutes. The solvents were removed in vacuo to give the title compound (1.17 g, 100%) as an oil.

Step C 5-(Benzyloxycarbonyl)pentylisocyanate (Compound 45)

According to the procedure described in Example 5, step G, aminocaproic acid, benzyl ester (1.17 g, 3.50 mmol) gave the title compound (0.922 g, 100%) as an oil.

Step D 4-[4-[[(4-Methyl)piperazin-1-yl]carbonyl]phenoxy]-1l-[5-(benzyloxycarbonyl)ethylaminocarbonyl]-3,3-diethyl-2-azetidinone (Compound 46)

According to the method of Shrenik et al (J. Med. Chem., 35, 3745–3754 (1992)), 4-[4-[[(4-methyl)piperazin-1-yl]carbonyl]phenoxy]-3,3-diethyl-2-azetidinone, prepared as in Example 5, step F, (316 mg, 0.91 mmol) and 5-(benzyloxycarbonyl)pentylisocyanate (922 mg, 3.50 mmol) gave, following purification by flash column chromatography (MeOH/EtOAc, 1:3), the title compound (0.53 g, 98%) as a pale yellow oil.

Step E 4-[4-[[(4-Methyl)piperazin-1-yl]carbonyl]phenoxy]-1-[5-(carboxy)pentylaminocarbonyl]-3,3-diethyl-2-azetidinone (Compound 47)

According to the procedure described in Example 2, step J, 4-[4-[[(4-methyl)piperazin-1-yl]carbonyl]phenoxy]-1-[5-(benzyloxycarbonyl)ethylaminocarbonyl]-3,3-diethyl-2-azetidinone (421 mg, 0.71 mmol) gave the title compound (320 mg, 90%) as a solid.

Step F Conjugate Between Chelate, 3,3,6,9,9-pentamethyl-6-aminomethyl-4,8-diazaundecane-2,10-dionedioxime and 4-[4-[[(4-Methyl)piperazin-1-yl]carbonyl]phenoxy]-1-[(5-carboxy)pentylaminocarbonyl]-3,3-diethyl-2-azetidinone (Compound 48)

According to the procedure described in Example 5, step J, 4-[4-[[(4-methyl)piperazin-1-yl]carbonyl]phenoxy]-1-[5-(carboxy)pentylaminocarbonyl]-3,3-diethyl-2-azetidinone (98 mg, 0.20 mmol) and 3,3,6,9,9-pentamethyl-6-aminomethyl-4,8-diazaundecane-2,10-dionedioxime (WO 95/19187, 76 mg, 0.24 mmol) gave, following purification by HPLC using system H, Example 12, the title compound (19.7 mg, 12%) as an oil.

Example 8

Conjugate Between Chelate, 3,3,6,9,9-Pentamethyl-6-aminomethyl-4,8-diazaundecane-2,10-dionedioxime and 4-[(4-Carboxy)phenoxy]-1-[benzylaminocarbonyl]-3,3-diethyl-2-azetidinone (Compound 49)

Step A Conjugate Between Chelate, 3,3,6,9,9-pentamethyl-6-aminomethyl-4,8-diazaundecane-2,10-dionedioxime and 4-[(4-carboxy)phenoxy]-1-[benzylaminocarbonyl]-3,3-diethyl-2-azetidinone (Compound 49)

According to the procedure described in Example 5, step J, 4-[(4-carboxy)phenoxy]-1-[benzylaminocarbonyl]-3,3-diethyl-2-azetidinone (J. Med. Chem., 35, 3745–3754 (1992), 100 mg, 0.25 mmol) and 3,3,6,9,9-pentamethyl-6-aminomethyl-4,8-diazaundecane-2,10-dionedioxime (WO 95/19187, 95 mg, 0.30 mmol) gave, following purification by HPLC using system H, Example 12, the title compound (18 mg, 10%) as an oil.

Example 9

Conjugate Between Chelate, 3,3,11,11-Tetramethyl-7-aminomethyl-4,7,10-triazatridecane-2,12-dionedioxime and 4-[4-[[(4-Methyl)piperazin-1-yl]carbonyl]phenoxy]-1-[(2-carboxy)ethylaminocarbonyl]-3,3-diethyl-2-azetidinone (Compound 51)

Step A 3,3,11,11-Tetramethyl-7-aminomethyl-4,7,10-triazatridecane-2,12-dionedioxime (Compound 50)

To tris (2-aminoethyl)amine (4 ml, 0.027 mol), acetonitrile (70 ml) and $NaHCO_3$ (7.4 g, 0.088 mol) was added 3-chloro-3-methyl-2-nitroso-butane (European Patent Application 0 179 608 A2, 2.5 g, 0.019 mol) in acetonitrile (50 ml) dropwise over 20 minutes. The mixture was stirred at room temperature for 20 hours, filtered and concentrated in vacuo. The crude product was purified by HPLC using system 1, Example 12 to give the title compound (700 mg, 8%) as an oil.

Step B Conjugate Between Chelate, 3,3,11,11-Tetramethyl-7-aminomethyl-4,7,10-triazatridecane-2,12-dionedioxime and 4-[4-[[(4-methyl)piperazin-1-yl]carbonyl]phenoxy]-1-[(2-carboxy)ethylaminocarbonyl]-3,3-diethyl-2-azetidinone (Compound 51)

To a mixture of 4-[4-[[(4-methyl)piperazin-1-yl]carbonyl]phenoxy]-1-[(2-carboxy)ethylaminocarbonyl]-3,3-diethyl-2-azetidinone, prepared as in example 6, step C, (100 mg, 0.22 mmol), 3,3,11,11-tetramethyl-7-aminomethyl-4,7,10-triazatridecane-2,12-dionedioxime (75 mg, 0.22 mmol) and HBTU (82 mg, 0.22 mmol) under nitrogen was added anhydrous DMF (1 ml). The mixture was stirred at room temperature and diisopropylethylamine (100 µl, 1.09 mmol) added and stirring continued for 40 hours. Following dilution with $MeOH/H_2O$, 1:1 (4 ml) the mixture was purified by HPLC using system H, Example 12 to give the title compound (54.2 mg, 32%) as an oil.

Example 10

Conjugate Between Chelate, 3,3,11,11-Tetramethyl-7-aminomethyl-4,7,10-triazatridecane-2,12-dionedioxime and 4-[(4-Carboxy)phenoxy]-1-[benzylaminocarbonyl]-3,3-diethyl-2-azetidinone (Compound 52)

Step A Conjugate Between Chelate, 3,3,11,11-tetramethyl-7-aminomethyl-4,7,10-triazatridecane-2,12-dionedioxime and 4-[(4-carboxy)phenoxy]-1-[benzylaminocarbonyl]-3,3-diethyl-2-azetidinone (Compound 52)

According to the procedure described in Example 9, step B, 4-[(4-carboxy)phenoxy]-1-[benzylaminocarbonyl]-3,3-diethyl-2-azetidinone (J. Med. Chem., 35, 3745–3754 (1992), 100 mg, 0.253 mmol) and 3,3,11,11-tetramethyl-7-aminomethyl-4,7,10-triazatridecane-2,12-dionedioxime, prepared as in Example 9, step A, (87 mg, 0.253 mmol) gave, following HPLC purification using system K, Example 12, the title compound (110 mg, 60%) as a solid.

Example 11

$^{99m}$Tc Labelling of Compounds 38, 42, 48, 49, 51 and 52

A solution of the compound for labelling in methanol (250 µg in 50 µl) was transferred to a $N_2$ filled 10 ml P6 vial followed by methanol (1 ml), deoxygenated saline (0.9% w/v, 1 ml) and aqueous sodium hydroxide (0.1 M, 18 µl). To this solution was added technetium-99m generator eluate (1 ml, approximately 0.5 GBq) and then aqueous $SnCl_2$ (0.1 ml, 10 µg). The labelling pH was 8.0–8.5. Vials were incubated at ambient temperature for 1 to 2 hours and the $^{99m}$Tc labelled product purified by HPLC using system A, Example 12, collecting the product into a plasma coated Schott vial containing unlabelled compound (200 µg in 250 µl methanol). The organic eluant was removed in vacuo and the sample diluted with buffer as described in Example 1, step G. The radiochemical purity of the purified compounds was measured using HPLC system A, Example 12 (results are in Table 22) and the thin layer chromatography (TLC) systems described below.

TLC i) ITLC SG 2 cm×20 cm eluted with 0.9% w/v saline ii) ITLC SG 2 cm×20 cm eluted with butan-2-one iii) Whatman No. 12 cm×20 cm eluted with 50:50 v/v acetonitrile:$H_2O$ where ITLC SG=instant thin layer chromatography, silica gel impregnated sheets supplied by Gelman.

Compounds 38, 42, 48, 49, 51 and 52 remain at, or close to, the origin in TLC system (i), between the origin and the solvent front in system (ii) and close to the solvent front in system (iii).

Example 12

HPLC Details

System A

Gilson 715 control software.

Gradient $T_{0'}$=100%A, 0%B, $T_{20'}$=0%A, 100%B.
Eluent A=0.1% TFA in $H_2O$
Eluent B=0.1% TFA in MeCN
Flow rate=1 ml/min
Column=150×3.9 mm Waters NovaPak C-18, 4 μ packing
Detection=UV (I=220 nm); activity (g)

System B
Gilson 715 control software.
Gradient $T_{0'}$=60%A, 40%B, $T_{20'}$=0%A, 100%B.
Eluent A=0.1% TFA in $H_2O$
Eluent B=0.1% TFA in MeCN
Flow rate=1 ml/min
Column=150×3.9 mm Waters NovaPak C-18, 4 μ packing
Detection=UV (I=220 nm); activity (g)

System C
Gilson 715 control software.
Gradient $T_{0'}$=60%A, 40%B, $T_{20'}$=0%A, 100%B.
Eluent A=Ammonium acetate buffer (pH 4, 0.05M)
Eluent B=Acetonitrile
Flow rate=1 ml/min
Column=150×3.9 mm Waters NovaPak C-18, 4 μ packing
Detection=UV, (I=220 nm); activity (g)

System D
Gilson 715 control software.
Isocratic; Eluent 18% B, 82% A
Eluent A=Na phosphate buffer (pH 6, 0.05M)
Eluent B=Acetonitrile
Flow rate=1 ml/min
Column Chromtech Chiral AGP 150×4 mm
Detection=UV (I=220 nm); activity (g)

System E
Gilson 715 control software.
Gradient $T_{0'}$=100%A, 0%B, $T_{20'}$=0%A, 100%B.
Eluent A=$H_2O$
Eluent B=MeCN
Flow rate=3 ml/min
Column=300×7.8 mm Waters NovaPak C-18, 6 μm packing
Detection=UV (I=220 nm or 254 nm)

System F
Gilson 715 control software.
Gradient=$T_{0'}$=100% A, 0%B, $T_{3'}$=100% A, 0%B $T_{20'}$=0%A, 100%B
Eluent A=sodium acetate buffer (pH 5.6, 50mM)
Eluent B=MeCN
Flow rate=1 ml/min
Column=150×3.9 mm Waters NovaPak C-18 4 μ packing
Detection=Activity=g and b⁻ scintillation detection (Packard Canberra Radiomatic 150TR scintillation analyser)

System G
Gilson 715 control software.
Isocratic; 18% B, 82% A
Eluent A=Na phosphate buffer (pH 6, 0.05M)
Eluent B=Acetonitrile
Flowrate=3 ml/min
Column=150×10.0 mm Chromtech Chiral AGP
Detection=UV (I=254 nm)

System H
Gilson 715 Software
Gradient=$T_{0'}$=100% A, 0% B, $T_{20'}$=0% A, 100% B
Eluent A=0.1% TEA in $H_2O$
Eluent B=0.1% TEA in MeCN
Flow rate=3 ml/min
Column=305×7 mm Hamilton PRP-1, 10 μ packing
Detection=UV (I=254 nm)

System I
Gilson 715 Software
Gradient=$T_{0'}$=100% A, $T_{30'}$=60% A, 40% B, $T_{40'}$=0% A, 100% B
Eluent A=2% $NH_3$ in $H_2O$
Eluent B=2% $NH_3$ in MeCN
Flow rate=3 ml/min
Column=305×7 mm Hamilton PRP-1, 10 μ packing
Detection=U.V. (I=210 nm)

System J
Gilson Unipoint Software
Gradient=$T_{0'}$=50% A, 50% B, $T_{15'}$=0% A, 100% B
Eluent A=0.2% TEA in $H_2O$
Eluent B=0.2% TEA in MeCN
Flow rate=3 ml/min
Column=NovaPak C18, 7.8×300 mm
Detection=U.V. (I=254 nm)

System K
Gilson 715 Software
Gradient=$T_{0'}$=70% A, 30% B, $T_{20'}$=0% A, 100% B
Eluent A=0.2% TEA in $H_2O$
Eluent B=0.2% TEA in MeCN
Flow rate=3 ml/min
Column=NovaPak C18, 7.8×300 mm
Detection=UV (I=254 nm)

TABLE 1

$^1$H NMR Data for Compounds 2,3,4 and 5.

| NMR data (ppm) | Compound 2 | Compound 3 | Compound 4 | Compound 5 |
|---|---|---|---|---|
| $CH_2CH_3$ | 0.93–1.10 | 0.91–1.16 | 0.93–1.08 | 0.80–1.71 |
| $CH_2CH_3$ | 1.55, 1.70–1.90 | 1.65–2.19 | 1.60–2.10 | 1.72–1.86 |
| $CH_2N$ | 4.40 | 4.40–4.58 | 4.35–4.50 | 4.45–4.56 |
| 4-H | 5.76 | 5.80 | 5.68 | 5.68 |
| NH | 6.85–6.96 | 6.90–7.00 | 6.85–7.00 | 6.90–7.00 |
| Ar | 7.07, 7.20, 7.68, 7.98 | 7.08, 7.22, 7.65, 8.03 | 7.00–7.13, 7.13–7.35, 7.35–7.50, 7.63–7.78 | 7.10–7.43 |
| $R_1$ = Ot-Bu | 1.55 | | | |
| $R_1$ = (4-methyl- | | | 2.30 ($NCH_3$), 2.30–2.60 | 2.31 ($NCH_3$), |

TABLE 1-continued

$^1$H NMR Data for Compounds 2,3,4 and 5.

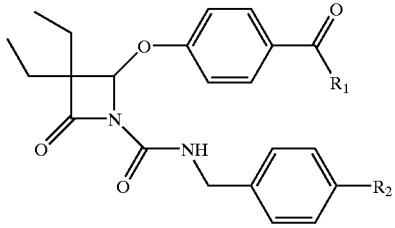

| NMR data (ppm) | Compound 2 | Compound 3 | Compound 4 | Compound 5 |
|---|---|---|---|---|
| piperazinyl) | | | (CH$_2$NCH$_3$), 3.40–3.90 | 2.31–3.50 (CH$_2$NCH$_3$) 3.25–3.90 (CH$_2$NCO) |
| | | | (CH$_2$NCO) | 0.80–1.71 |
| R$_2$ = Sn(n-Bu)$_3$ | | | | |

TABLE 2

$^1$H NMR Data for Compounds 1,6,7,8 and 9.

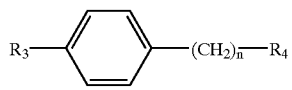

| NMR data (ppm) | Compound 1 | Compound 6 | Compound 7 | Compound 8 | Compound 9 |
|---|---|---|---|---|---|
| CH$_2$R$_4$ | 4.45 | 2.64–2.76 | 2.73 | 2.84–2.92 | 2.78–2.93 |
| CH$_2$Ar | | 3.20–3.40 | 3.33 | 3.08–3.16 | 3.34–3.88 |
| Ar | 7.00–7.10, 7.70 | 6.80, 7.00 | 6.92, 7.10 | 6.98, 7.20 | 6.81–7.93 |
| R$_3$ = OH | | 7.44 | | | |
| R$_3$ = OCH$_2$Ar | | | 5.04 (CH$_2$), 7.32–7.44 (Ar) | 5.08 (CH$_2$), 7.28–7.44 (Ar) | 5.06 (CH$_2$), 6.81–7.93 (Ar) |
| R$_4$ = NHCO$_2$t-Bu | | 1.48 (t-Bu), 4.76 (NH) | 1.43 (t-Bu), 4.54 (NH) | | |

TABLE 3

$^1$H NMR Data for Compounds 10 and 11.

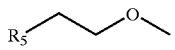

| NMR data (ppm) | Compound 10 | Compound 11 |
|---|---|---|
| OCH$_3$ | 3.32 | 3.20–3.28 |
| CH$_2$O | 3.60 | 3.20–3.28 |
| CH$_2$R$_5$ | 4.16 | 2.40 |
| R$_5$ = OTs (ArCH$_3$) | 2.45 (CH$_3$), 7.38 and 7.80 (Ar) | |
| R$_5$ = Ph$_3$CS | | 7.20–7.44 |

TABLE 4

$^1$H NMR Data for Compound 12.

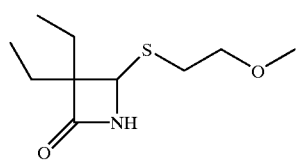

| NMR data (ppm) | Compound 12 |
|---|---|
| CH$_2$CH$_3$ | 0.90–1.10 |
| CH$_2$CH$_3$ | 1.60–1.92 |
| CH$_2$ × 2 | 2.74–2.84 and 3.49–3.68 |
| OCH$_3$ | 3.38 |
| 4-H | 4.49 |
| NH | 6.58 |

TABLE 5

$^1$H NMR data for Compounds 18 and 19

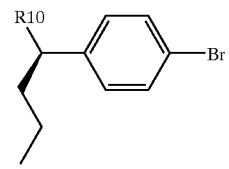

| NMR data (ppm) | Compound 18 | Compound 19 |
|---|---|---|
| CH$_3$ | 0.94 | 0.92 |
| (CH$_2$)$_2$ | 1.19–2.08 | 1.24–1.86 |
| CHR$_{10}$ | 3.52 | 4.57 |
| Ar | 7.17, 7.44 | 7.17, 7.48 |

TABLE 6

$^1$H NMR data for Compounds 13, 14, 15, 16 and 17.

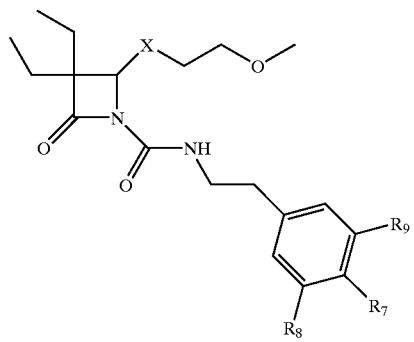

| NMR data (ppm) | Compound 13 | Compound 14 | Compound 15 | Compound 16 | Compound 17 |
|---|---|---|---|---|---|
| $CH_2CH_3$ | 0.96 | 0.99–1.10 | 0.98–1.10 | 1.00–1.10 | 0.90–1.00 |
| $CH_2CH_3$ | 1.04, 1.67–1.90 | 1.66–2.40 | 1.63–2.40 | 1.40–1.60 | 1.60–2.40 |
| $CH_2Ar$ | 2.75 | 2.80 | 2.76 | 2.70 | 2.60–2.70 |
| $XCH_2CH_2$ | 3.20, 3.25–3.72 | 3.09, 3.70–3.76, 3.91–4.00, 4.53 | 3.08–3.16, 3.67–3.76, 3.90–4.00, 4.41–4.57 | 3.00–3.10, 3.70–3.78, 3.90–4.00, 4.40–4.60 | 3.00–3.10, 3.60–3.70, 3.90–4.00, 4.50–4.60 |
| $CH_2N$ | 3.25–3.72 | 3.40–3.53 | 3.43–.51 | 3.40–3.50 | 3.40–3.50 |
| $OCH_3$ | 3.25–3.72 | 3.40–3.53 | 3.40 | 3.40–3.50 | 3.40 |
| 4-H | 5.00–5.04 | 5.11 | 5.11 | 5.10 | 5.10 |
| NH | 6.63 | 6.65 | 6.67 | 6.67 | 6.60 |
| Ar | 6.92, 7.13 | 6.93, 7.12 | 6.78, 7.03 | 6.90, 7.07, 7.50 | 7.45 |
| $R_7 =$ $OCH_2Ar$ | 5.00–5.04 ($CH_2$), 7.29–7.46 (Ar) | 5.04 ($CH_2$), 7.32–7.42 (Ar) | | | |
| $R_7 = OH$ | | | | | 5.37 |

TABLE 7

$^1$H NMR data for Compounds 20, 21, 22 and 23

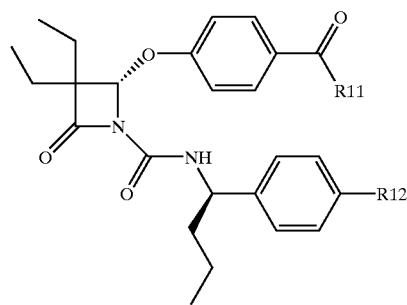

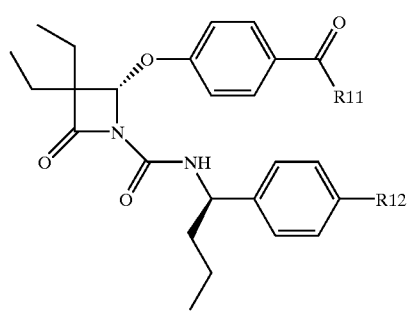

| NMR data (ppm) | Compound 20 | Compound 21 | Compound 22 | Compound 23 |
|---|---|---|---|---|
| $CH_3 \times 3$ | 0.83–1.05 | 0.89–1.06 | 0.89–1.08 | 0.87–1.66 |
| $CH_2$ | 1.22–1.41 | 1.19–1.39 | 1.24–1.40 | 0.87–1.66 |
| $CH_2 \times 3$ | 1.68–2.05 | 1.66–2.06 | 1.68–2.06 | 1.71–2.03 |
| CHNH | 4.79 | 4.81 | 4.79 | 4.85 |
| 4-H | 5.65 | 5.73 | 5.61 | 5.60 |
| NH | 6.89 | 6.92 | 6.94 | 6.97 |
| Ar | 7.16, 7.44, 7.94 | 7.13–7.23, 7.48, 8.05 | 7.16, 7.24, 7.38, 7.47 | 7.21–7.50 |
| $R_{11} = $ Ot-Bu | 1.59 | | | |
| $R_{11} = $ OH | | 7.62 | | |
| $R_{11} = $ (4-methyipipera-zinyl) | | | 2.31 ($CH_3$), 2.40 ($CH_2$), 3.71 ($CH_2$) | 2.31 ($CH_3$), 2.40 ($CH_2$), 3.58–3.87 ($CH_2$) |
| $R_{12} = $ Sn(n-Bu)$_3$ | | | | 0.87–1.66 |

TABLE 8

$^1$H NMR data for compound 25

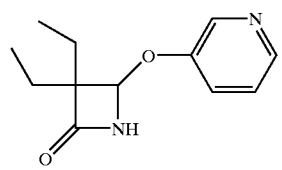

| NMR data (ppm) | Compound 25 |
|---|---|
| CH$_3$ × 2 | 0.95–1.09 |
| CH$_2$ × 2 | 1.71–2.00 |
| 4-H | 5.36 |
| Pyr | 7.27, 8.27 |
| NH | 7.26 |

TABLE 9

$^1$H NMR data for Compounds 29, 30, 31 and 35

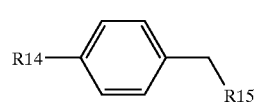

| NMR data | Compound 29 | Compound 30 | Compound 31 | Compound 35 |
|---|---|---|---|---|
| CH$_2$R$_{15}$ | 4.37 | 4.34–4.35 | 4.13 | 4.50 |
| Ar | 7.37, 8.05 | 7.32–7.45, 8.03 | 7.30–7.44, 7.96 | 7.25–7.42, 8.01 |
| R$_{14}$ = CO$_2$CH$_2$Ar | | 5.34 (CH$_2$), 7.32–7.45 (Ar) | 5.29 (CH$_2$), 7.30–7.44 (Ar) | 5.31 (CH$_2$), 7.25–7.42 (Ar) |
| R$_{15}$ = NHCO$_2$t-Bu | 1.45 (t-Bu), 4.93 (NH) | 1.42 (t-Bu), 4.92 (NH) | | |

TABLE 10

$^1$H NMR data for compounds 26 and 27

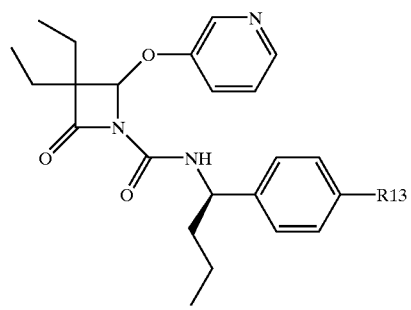

| NMR data (ppm) | Compound 26 | Compound 27 |
|---|---|---|
| CH$_3$ × 2 | 0.84–2.04 | 0.86–1.58 |
| CH$_2$ × 2 | 0.84–2.04 | 1.72–2.09 |
| CH$_2$CH$_2$CH$_3$ | 0.84–2.04 | 1.58–0.86 (CH$_3$ + CH$_2$), 1.72–2.09 (CH$_2$) |
| CHNH | 4.78 | 4.81 |
| 4-H | 5.55 | 5.54 |
| NH | 6.91–7.49 | 6.94 |
| Ar | 6.91–7.49 | 7.21–7.28, 7.42 |
| Pyr | 6.91–7.49, 7.73, 8.31–8.44 | 7.21–7.28, 7.78, 8.33, 8.44 |
| R$_{13}$ = Sn(n-Bu)$_3$ | | 0.86–1.58 |

TABLE 11

$^1$H NMR data for compounds 32 and 33

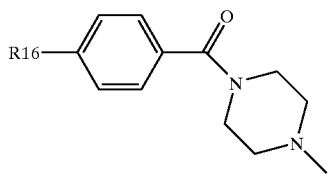

| NMR data (ppm) | Compound 32 | Compound 33 |
|---|---|---|
| NCH$_3$ | 2.28 | 2.33 |
| 2 × CH$_2$NCH$_3$ | 2.38–2.46 | 2.48 |
| 2 × CH$_2$NCO | 3.54–3.75 | 3.63 |
| Ar | 6.97, 7.30–7.45 | 6.84, 7.28 |
| R$_{16}$ = OCH$_2$Ar | 5.08 (CH$_2$), 7.30–7.45 (Ar) | |
| R$_{16}$ = OH | | 4.88 |

TABLE 12

$^1$H NMR data for compound 34

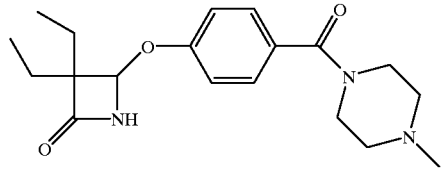

| NMR data (ppm) | Compound 34 |
|---|---|
| CH$_3$ × 2 | 1.02–1.11 |
| CH$_2$ × 2 | 1.72–2.00 |
| NCH$_3$ | 2.33 |
| 2 × CH$_2$NCH$_3$ | 2.44 |
| 2 × CH$_2$NCO | 3.44–3.81 |
| 4-H | 5.35 |
| NH | 6.78 |
| Ar | 6.87, 7.39 |

TABLE 13

<sup>1</sup>H NMR data for compounds 36, 37 and 38

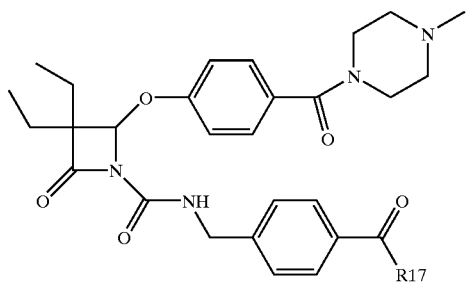

| NMR data (ppm) | Compound 36 | Compound 37 | Compound 38 |
|---|---|---|---|
| $CH_3 \times 2$ | 0.90–1.02 | 0.98–1.09 | 0.97–1.08 |
| $CH_2 \times 2$ | 1.68–1.98 | 1.79–2.00 | 1.73–2.03 |
| $NCH_3$ | 2.25 | 2.63 | 2.32 |
| $2 \times CH_2NCH_3$ | 2.33 | 2.88 | 2.42 |
| $2 \times CH_2NCO$ | 3.33–3.77 | 3.93–4.06 | 3.45–3.83 |
| $NCH_2Ar$ | 4.47 | 4.54 | 4.52 |
| 4-H | 5.63 | 5.71 | 5.68 |
| urea NH | 6.92 | 7.04 | 7.00 |
| Ar | 7.17, 7.25–7.37, 7.97 | 7.28, 7.37–7.43, 8.04 | 7.25, 7.33–7.42, 7.75 |
| $R_{17} = OCH_2Ar$ | 5.28 ($CH_2$), 7.25–7.37 (Ar) | | |
| $R_{17}$ = Ligand 1 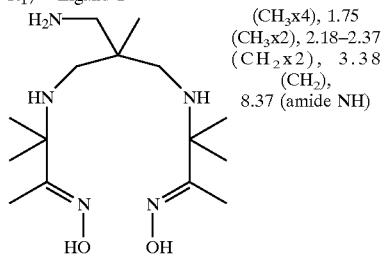 | | ($CH_3$x4), 1.75 ($CH_3$x2), 2.18–2.37 ($CH_2$x2), 3.38 ($CH_2$), 8.37 (amide NH) | 0.92 ($CH_3$), 1.23 |

TABLE 14

<sup>1</sup>H NMR data for Compound 39

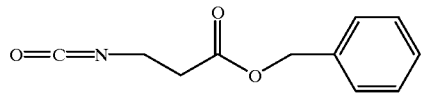

| NMR data (ppm) | Compound 39 |
|---|---|
| $CH_2CO_2$ | 2.58 |
| $CH_2N$ | 3.51 |
| $CH_2Ar$ | 5.17 |
| Ar | 7.36 |

TABLE 15

<sup>1</sup>H NMR data for Compounds 43, 44 and 45

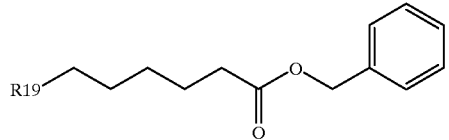

| NMR data (ppm) | Compound 43 | Compound 44 | Compound 45 |
|---|---|---|---|
| $CH_2 \times 3$ | 1.21–1.71 | 1.34–1.73 | 1.40–1.80 |
| $CH_2CO_2$ | 2.35 | 2.41 | 2.45 |
| $CH_2R_{19}$ | 3.08 | 2.90 | 3.35 |
| $CH_2Ar$ | 5.10 | 5.11 | 5.68 |
| Ar | 7.30 | 7.36 | 7.18–7.33 |
| $R_{19} = NHCO_2$t-Bu | 1.46 (t-Bu), 4.46 (NH) | | |

TABLE 16
¹H NMR data for Compounds 40, 41, 42 and 51
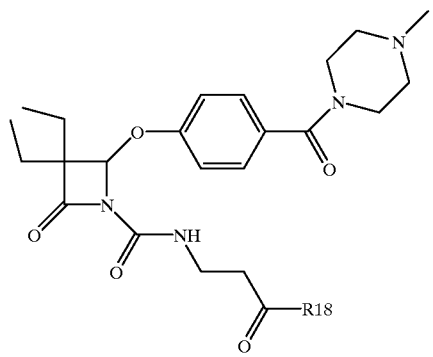
| NMR data | Compound 40 | Compound 41 | Compound 42 | Compound 51 |
|---|---|---|---|---|
| 2 x $CH_3$ | 0.94–1.04 | 0.95–1.06 | 0.94–1.07 | 0.95–1.06 |
| 2 x $CH_2$ | 1.71–1.97 | 1.76–1.99 | 1.67–2.01 | 1.79–2.01 |
| $NCH_3$ | 2.34 | 2.45 | 2.33 | 2.33 |
| 2 x $CH_2NCH_3$ | 2.44–2.56 | 2.72 | 2.20–2.49 | 2.46–2.58 |
| $CH_2CO$ | 2.61 | 2.54 | 2.20–2.49 | 2.46–2.58 |
| $CH_2NCON$ | 3.51 | 3.54 | 3.49–3.72 | 3.21–3.83 |
| 2 x $CH_2NCO$ | 3.49–3.70 | 3.78 | 3.49–3.72 | 3.21–3.83 |
| 4-H | 5.85 | 5.75 | 5.67 | 5.65 |
| urea NH | | 7.20 | 7.07 | 7.14 |
| Ar | 7.23–7.43 | 7.25, 7.41 | 7.25, 7.40 | 7.22, 7.39 |
| $R_{18}$ = $OCH_2Ar$ | 5.10 ($CH_2$), 7.23–7.43 (Ar) | | | |
| $R_{18}$ = OH | | | 10.78 | |
| $R_{18}$ = [structure below] | | | | 0.84 ($CH_3$), 1.22 ($CH_3$x4), 1.84 ($CH_3$x2), 2.20–2.49 ($CH_2$x2), 3.20 ($CH_2$), 7.79 (amide NH) |
| $R_{18}$ = [structure below] | | | | 1.25 ($CH_3$x4), 1.83 ($CH_2$x2), 2.46–2.58 ($CH_2$x5), 3.21–3.83 ($CH_2$) |
TABLE 17
¹H NMR data for Compounds 46, 47 and 48

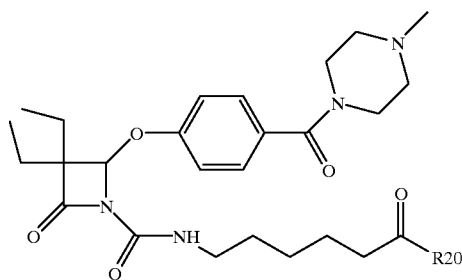

| NMR data (ppm) | Compound 46 | Compound 47 | Compound 48 |
|---|---|---|---|
| $CH_3CH_2$ x 2 | 0.88–1.02 | 0.95–1.07 | 0.89–1.01 |
| $CH_2$ x 3 | 1.25–1.65 | 1.30–1.68 | 1.25–1.60 |
| $CH_3CH_2$ x 2 | 1.69–1.98 | 1.72–2.02 | 1.67–1.95 |
| $NCH_3$ | 2.23 | 2.37 | 2.25 |
| $CH_2NCH_3$ x 2 | 2.29–2.46 | 2.55 | 2.35 |
| $CH_2CO$ | 2.29–2.46 | 2.32 | 2.00–2.21 |
| $CH_2NCON$ | 3.21 | 3.18–3.33 | 3.19–3.25 |
| $CH_2NCO$ x 2 | 3.35–3.79 | 3.50–3.88 | 3.49–3.76 |
| 4-H | 5.60 | 5.65 | 5.57 |
| NH | 6.52 | 6.55 | 6.52 |
| Ar | 7.19, 7.23–7.38 | 7.23, 7.37 | 7.17, 7.32 |
| $R_{20}$ = $OCH_2Ar$ | 5.04 ($CH_2$), 7.23–7.38 (Ar) | | |

$R_{20}$ = Ligand1

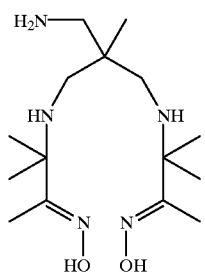

0.79 ($CH_3$),
1.18 ($CH_3$x4),
1.75 ($CH_3$x2),
2.00–2.21 ($CH_2$x2),
3.09 ($CH_2$)

TABLE 18

$^1$H NMR data for Compounds 49 and 52

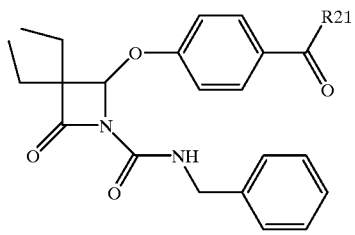

| NMR data (ppm) | Compound 49 | Compound 52 |
|---|---|---|
| $CH_2CH_3$ x 2 | 0.90–1.26 | 0.94–1.11 |
| $CH_2CH_3$ x 2 | 1.66–1.91 | 1.69–2.01 |
| $CH_2Ar$ | 4.41 | 4.48 |
| 4-H | 5.66 | 5.71 |
| NH | 6.84 | 6.90 |
| Ar | 7.16–7.31, 7.67 | 7.18, 7.22–7.36, 7.82 |

$R_{21}$ = Ligand1

TABLE 18-continued $^1$H NMR data for Compounds 49 and 52

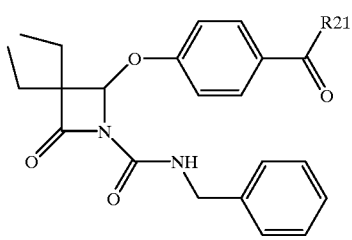

| NMR data (ppm) | Compound 49 | Compound 52 |
|---|---|---|
| | | 0.84 ($CH_3$), 2.19 ($CH_3$ x 4), 1.69 ($CH_3$ x 2), 1.95–2.19 ($CH_2$ x 2), 3.33 ($CH_2$), 9.72 (OH x 2) |

$R_{21}$ = Ligand2

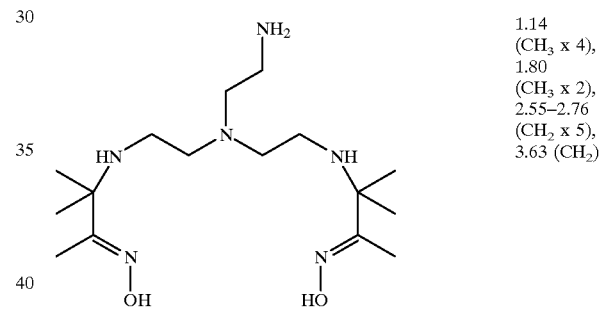

1.14 ($CH_3$ x 4),
1.80 ($CH_3$ x 2),
2.55–2.76 ($CH_2$ x 5),
3.63 ($CH_2$)

TABLE 19

NMR data for compound 50

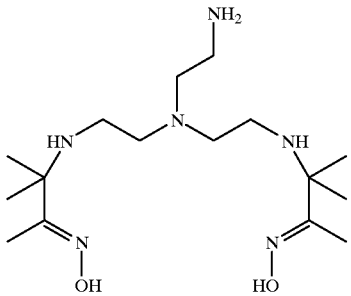

| NMR data (ppm) | Compound 50 |
|---|---|
| 4 x $CH_3$ | 1.05 |
| 2 x $CH_3$ | 1.71 |
| 6 x $CH_2$ | 2.25–2.64 |

TABLE 20

RCP of $^{123}$I-compounds before and after testing

| Compound | Pre-testing | | | Post-testing | | |
|---|---|---|---|---|---|---|
| | Time (min) | Retention time (min) | RCP | Time (min) | Retention time (min) | RCP |
| [$^{123}$I]-4 | 119 | 7.6 | >95% | 166 | 7.6 | >90% |
| [$^{123}$I]-4a | — | — | — | 371 | ca 14.0[1] | >95% |
| [$^{123}$I]-4b | — | — | — | 428 | ca 18.0[1] | >95% |
| [$^{123}$I]-16 | 101 | 17.3 | >95% | 154 | 17.3 | >95% |
| [$^{123}$I]-17 | 111 | 19.1 | >95% | 304 | 19.0 | >95% |

[1]significant variation in retention time observed according to ambient HPLC conditions

TABLE 21

HPLC retention times ($t_R$) for $^{123}$I and $^{127}$I analogues

| Compound | $t_R$ $^{123}$I compound[1] (g-detector) (min) | $t_R$ $^{127}$I compound[1] (UV detector) (min) |
|---|---|---|
| 4 | 6.6 | 6.4 |
| 16 | 17.3 | 17.1 |
| 17 | 19.1 | 18.9 |

[1]difference in $t_R$ due to void volume differences

TABLE 22

RCP of $^{99m}$Tc-labelled compounds before testing

| Compound | Time (min) after HPLC purification | Retention time (min) | RCP |
|---|---|---|---|
| $^{99m}$Tc-38 | 60 | 15.5 | >85% |
| $^{99m}$Tc-42 | 30 | 14.1 | >85% |
| $^{99m}$Tc-48 | 60 | 15.1 | >85% |
| $^{99m}$Tc-49 | 30 | 18.3 | >85% |
| $^{99m}$Tc-51 | 60 | 12.5 | >85% |
| $^{99m}$Tc-52 | 60 | 17.1 | >85% |

Example 13

Measurement of HLE Inhibition Potency

Inhibitor potency against HLE is described by the parameter $k_{inact}/K_i$ as previously reported [Knight et al., Biochem., 8160–8170, (1992)]. Lyophilised enzyme was reconstituted with TrisHCl buffer, 100 mM, 0.5M NaCl at 0.05 units/ml (approximately nanomolar concentration) in a final reaction volume of 1 ml to which was added methoxysucc-ala-ala-pro-val-pNA substrate (1 mM) and the elastase inhibitor dissolved in DMSO. The reaction was monitored by detecting the change of absorbance at 410 nm (hydrolysis of the substrate releasing p-nitroaniline) over a timescale of 25 minutes. Values of $k_{inact}/K_i$ were estimated according to the Knight et al method.

Results are given in Tables 23 and 24.

Example 14

Measurement of In Vitro Human Cell Selectivity in Isolated White Blood Cells, in Mixed White Plus Red Cells and in Whole Blood Isolated Human White Cells Fresh blood (30–120 ml) was anticoagulated with 1.5% ACD solution and sedimented by addition of 2 ml Hespan per 10 ml blood for 90 minutes at room temperature. The leucocyte rich platelet rich plasma supernatant was removed and centrifuged at 150 g for 5 minutes, yielding a leucocyte rich pellet and platelet rich plasma (PRP). The PRP was centrifuged at 4000 g to pellet the platelets leaving a cell free plasma (CFP). The leucocyte pellet was resuspended in a 50:50 mixture of HBSS and CFP and incubated with the radioactive compound for 30 minutes at 37° C. Free radioactive material was then removed from the cells by addition of an excess of HBSS:CFP and centrifugation of the leucocytes at 150 g for 7 minutes. The supernatant and cell pellet were taken for radioactive counting for calculation of percentage cell uptake. The distribution of radioactivity within the cell pellet was assessed by separation of the cell types using Percoll density gradient centrifugation (38%, 55% and 73% Percoll in HBSS step gradients). The residual plasma and free activity was recovered from the top of the gradient, the mononuclear cells (lymphocytes and monocytes) from the interface between 38% and 55%, and the granulocytes were recovered from the interface between 55% and 73% Percoll. Results are given in Table 23.

Mixed Human Red/White Cells.

The radioactive compound was also incubated with an isolated leucocyte preparation to which an erythrocyte fraction had been added back. The packed erythrocytes obtained after blood sedimentation were washed twice with HBSS and then resuspended in their original blood volume with HBSS. Leucocytes obtained from 30 ml blood were resuspended in 0.5 ml erythrocyte suspension and 0.5 ml CFP. The cell suspension was then incubated with compound as above. Analysis of the distribution of activity in the cell pellet in the presence of red blood cells was carried out using Ficoll-Hypaque discontinuous density gradients (densities 1.04, 1.077 and 1.119 g/ml Histopaque steps). Results are given in Table 23.

Human Whole Blood.

The radioactive compound was added to 1 ml whole blood anticoagulated with ACD and incubated at 37° C. for 1 hour. The blood was diluted with HBSS and the cellular component separated by centrifugation. Distribution of activity within the cellular pellet was assessed by separation of cell fractions on Ficoll-Hypaque gradients as above. Results are given in Table 23.

TABLE 23

Comparison of potency with in vitro human blood cell uptake

| Compound | Potency (M/sec) | WHITE CELLS | | WHITE AND RED CELLS | | | WHOLE BLOOD | | |
|---|---|---|---|---|---|---|---|---|---|
| | | Mon. | Gran. | Mon. | Gran. | Eryth. | Mon. | Gran. | Eryth. |
| 4 | 32,000 | 2.0 | 25.7 | 3.4 | 14.4 | 14.2 | 3.9 | 5.0 | 6.5 |
| 4a | 63,000 | 14.3 | 68.6 | 14.6 | 53.2 | 8.4 | — | — | — |
| 4b | 1350 | 0.9 | 4.8 | 3.8 | 3.3 | 1.6 | — | — | — |

TABLE 23-continued

Comparison of potency with in vitro human blood cell uptake

| Compound | Potency (M/sec) | WHITE CELLS | | WHITE AND RED CELLS | | | WHOLE BLOOD | | |
|---|---|---|---|---|---|---|---|---|---|
| | | Mon. | Gran. | Mon. | Gran. | Eryth. | Mon. | Gran. | Eryth. |
| 16 | 2,700 | 0.0 | 0.55 | 0.6 | 0.3 | 0.6 | 0.6 | 0.2 | 0.2 |
| 17 | 600 | 0.0 | 0.4 | — | — | — | — | — | — |
| 24 | 2830000 | 3.4 | 83.2 | 4.0 | 40.4 | 41.7 | 13.6 | 24.3 | 16.6 |
| 28 | 650000 | 14.8 | 67.4 | 14.9 | 41.9 | 17.5 | — | — | — |
| 38 | 58500 | 8.5 | 75.5 | 6.7 | 32.5 | 28.4 | — | — | — |
| 42 | 1400 | 1.2 | 8.4 | 6.9 | 2.5 | 18.9 | — | — | — |
| 48 | 5500 | 7.3 | 64.5 | 7.2 | 16.2 | 38.7 | 22.7 | 10.6 | 9.17 |
| 49 | 20000 | 10.1 | 47.3 | 13.9 | 17.5 | 18.0 | 24.6 | 6.9 | 14.3 |
| 51 | 2500 | 0.4 | 3.9 | 13.4 | 1.9 | 11.2 | 28.7 | 1.7 | 0.8 |
| 52 | 7800 | 0.8 | 1.9 | 8.2 | 1.8 | 7.1 | 10.9 | 9.1 | 37.4 | where:
Mon. = monocytes + lymphocytes
Gran. = granulocytes
Eryth. = erythrocytes
Figures are % uptake in each cell fraction Example 15

In Vivo Biodistribution of Radiolabelled Elastase Inhibitors in Rats Bearing Experimental Abscesses The model: into the right gracilis (thigh) muscle of male Wistar rats (250–325 g) were injected 1 ml/kg of an *E. coli* suspension containing >> 5×10$^8$/ml organisms. Over the next 24 hours a pustulent abscess developed at the site of the popliteum lymph node with the surrounding muscle also showing signs of inflammation. These visible observations were confirmed by histology.

Validation: the model was validated for use in the development of diagnostic imaging agents of infection/inflammation by the intravenous injection of $^{99m}$Tc-HMPAO ex-vivo labelled human wbc or $^{67}$Ga-citrate when the abscesses were 24 hours old. Animals were dissected between 4 and 24 hours after injection. $^{99m}$Tc-labelled red blood cells were used as a negative control.

Screening in *E. coli* infected rats: 0.2–10 MBq of either $^{123}$I- or $^{99m}$Tc-labelled elastase inhibitors diluted in phosphate buffered saline (pH=7.4) were injected intravenously into the caudal vein of 24 hour abscess bearing rats. The animals were sacrificed at either 4 or 24 hours post injection and relevant tissues dissected.

Screening of Ex vivo labelled human leucocytes in *E. coli* infected rats: A mixed population of human leucocytes was incubated with elastase inhibitor for 30 minutes at 37° C. The cells were then spun down and resuspended in a known volume of rat plasma for intravenous injection into rats bearing a 24 hour old abscess. Animals were dissected at 4 and 24 hours post injection. Results are shown in Table 24.

Example 16

In Vivo Stability of Iodinated HLE Inhibitors

The in vivo stability of radioiodinated HLE inhibitors was monitored by determination of the percentage uptake in the thyroid as a function of time after administration. Thus radioiodinated compounds and $^{123}$I free iodide were injected into male Wistar rats. The percentage of injected dose distributing to the thyroid was calculated by dissection at 4 and 24 hours post injection and counting. Results are given in Table 25.

Example 17

In-vitro Forming Plasma Clot Assay

1 μM of a potent ($K_{inact}/K_i$>3000000 M/sec) β-lactam elastase inhibitor was added to aliquots of human plasma pooled from 6 volunteers. The test sample contained plasma with added granulocytes (see example 14 for isolation method) to a final concentration of 10$^6$/ml and 2 volumes of 50 mM Tris buffered saline containing 15 mM calcium chloride. The control sample consisted of plasma and Tris buffer without calcium. Clots were allowed to form for 60 minutes after the addition of 4 units of bovine thrombin and a roughened glass rod to induce clot formation.

After incubation (c.20° C.) the reaction was discontinued by the addition of 400 μL cold 33.5mM ethylenediaminetetraacetic acid disodium salt. Solutions were filtered by the use of a vacuum manifold onto 0.45 μm nitrocellulose filters (pre-soaked in 1.5% bovine serum albumin/Tris buffered saline, pH 7.5 containing 0.1% Tween 20) and washed with the same buffer minus BSA.

The fraction of radioactivity retained on the filter, after subtraction of non-specific binding is a measure of % incorporation into the filtered clots.

TABLE 24

Screening of elastase inhibitors by direct intravenous injection and injection of ex vivo labelled human leucocytes

| Compound | $k_{inact}/Ki$ (human elastase) | Infected/normal | | Infected/blood | | Relative conc. In infected area | |
|---|---|---|---|---|---|---|---|
| Directly injected [$^{123}$I]-4 | 32000 | 4 hrs | 1.3 | 4 hrs | 0.62 | 4 hrs | 0.51 |
|  |  | 24 hrs | 1.3 | 24 hrs | 0.51 | 24 hrs | 0.12 |
| Directly injected [$^{123}$I]-4a | 36000 | 4 hrs | 1.0 | 4 hrs | 0.62 | 4 hrs | 0.52 |
|  |  | 24 hrs | 1.6 | 24 hrs | 0.53 | 24 hrs | 0.28 |
| Ex vivo labelled [$^{123}$I]-4 | 32000 | 4 hrs | 1.5 | 4 hrs | 0.61 | 4 hrs | 0.7 |
|  |  | 24 hrs | 1.9 | 24 hrs | 0.75 | 24 hrs | 0.19 |
| Directly injected [$^{123}$I]-24 | 2830000 | 4 hrs | 1.3 | 4 hrs | 1.3 | 4 hrs | 0.38 |
|  |  | 24 hrs | 1.1 | 24 hrs | 0.9 | 24 hrs | 0.16 |
| Ex vivo labelled [$^{123}$I]-24 | 2830000 | 4 hrs | 1.3 | 4 hrs | 0.9 | 4 hrs | 0.53 |
|  |  | 24 hrs | 1.3 | 24 hrs | 0.9 | 24 hrs | 0.20 |
| Directly injected [$^{123}$I]-28 | 650000 | 4 hrs | 1.3 | 4 hrs | 1.1 | 4 hrs | 0.22 |
|  |  | 24 hrs | 1.2 | 24 hrs | 1.2 | 24 hrs | 0.12 |
| Ex vivo labelled [$^{123}$I]-28 | 650000 | 4 hrs | 1.5 | 4 hrs | 0.9 | 4 hrs | 0.45 |
|  |  | 24 hrs | 1.2 | 24 hrs | 0.9 | 24 hrs | 0.16 |
| Directly injected [$^{99m}$Tc]-38 | 58500 | 4 hrs | 1.4 | 4 hrs | 1.0 | 4 hrs | 0.08 |
|  |  | 24 hrs | nc | 24 hrs | 1.4 | 24 hrs | 0.14 |
| Directly injected [$^{99m}$Tc]-42 | 1400 | 4 hrs | 2.7 | 4 hrs | 0.9 | 4 hrs | 0.10 |
|  |  | 24 hrs | nc | 24 hrs | 2.2 | 24 hrs | 0.11 |
| Directly injected [$^{99m}$Tc]-48 | 5500 | 4 hrs | 1.7 | 4 hrs | 1.0 | 4 hrs | 0.07 |
|  |  | 24 hrs | nc | 24 hrs | 2.5 | 24 hrs | 0.08 |
| Directly injected [$^{99m}$Tc]-49 | 20000 | 4 hrs | 1.5 | 4 hrs | 0.5 | 4 hrs | 0.05 |
|  |  | 24 hrs | 2.0 | 24 hrs | 1.5 | 24 hrs | 0.16 |
| Ex vivo labelled $^{99m}$Tc HMPAO wbc | — | 4 hrs | 3.3 | 4 hrs | 0.4 | 4 hrs | 0.2 |
|  |  | 24 hrs | 4.0 | 24 hrs | 0.7 | 24 hrs | 0.1 |
| Directly injected $^{99m}$Tc-RBC's | — | 4 hrs | 0.6 | 4 hrs | <0.01 | 4 hrs | 0.1 |
|  |  | 24 hrs | 0.8 | 24 hrs | <0.01 | 24 hrs | 0.1 |
| $^{67}$Ga-citrate | — | 24 hrs | 2.2 | 24 hrs | 3.9 | 24 hrs | 0.9 |
|  |  | 48 hrs | 3.9 | 48 hrs | 9.7 | 48 hrs | 1.1 |

Parameters are defined as follows:
1) Infected/normal ratio: the ratio of the % injected dose identified (id) per gram of tissue in the infected area relative to that seen in a control area taken from the thigh of the contralateral limb.
2) Infected/blood ratio: the ratio of %/g in the infected area relative to activity in blood. A low ratio indicates that the accumulation in the infected area could be masked by the activity in the blood pool.
3) The relative concentration of agent in the infected area. This can be defined as the % of the injected dose in a % body weight. For example 1% of the injected dose in a tissue which is 1% of the body weight would have a relative concentration of 1.

TABLE 25

% Thyroid uptake following i.v. injection of free [$^{123}$I]-iodide and $^{123}$I-labelled compounds

| Compound | % dose in Thyroid | |
|---|---|---|
|  | 4 hours | 24 hours |
| [$^{123}$I]-iodide | 6.8 | 22.2 |
| [$^{123}$I]-4 | 0.1 | 0.9 |
| [$^{123}$I]-4a | 0.1 | 0.3 |
| [$^{123}$I]-16 | 0.3 | 2.4 |
| [$^{123}$I]-24 | 0.2 | 0.6 |

What is claimed is:

1. A human leucocyte elastase (HLE) inhibitor labelled with a detectable moiety where the inhibitor is synthetic and has a molecular weight of less than 2000, and the detectable moiety is chosen from the group consisting of a radioactive isotope, a paramagnetic ion, a radiopaque compound and an ultrasound contrast agent.

2. The labelled HLE inhibitor of claim 1 where the radioactive isotope is a gamma emitter.

3. The labelled HLE inhibitor of claim 1 where the radioactive isotope is $^{123}$I, $^{99m}$TC, $^{111}$In or $^{67}$Ga.

4. The labelled HLE inhibitor of claim 1 where the inhibitor is β-lactam.

5. The labelled HLE inhibitor of claim 1 where the inhibitor is an ynenol lactone.

6. The labelled HLE inhibitor of claim 4 where the β-lactam has the general formula:

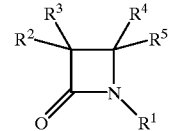

wherein $R^1$ is $R^8$, $XR^8$, $(CRR)_n(C=X)R^8$ or $(C=X)NR^8_2$

X is O or S n is 0-3, $R^8$ is H, OH, a substituted or unsubstituted $C_{3-12}$ carbocyclic or heterocyclic ring which may be saturated or unsaturated, $C_{1-10}$ alkyl, $C_{3-12}$ aryl, $C_{4-12}$ alkylaryl, $C_{2-10}$ alkenyl, $C_{2-10}$ alkynyl, $C_{1-10}$ alkoxy, $C_{1-10}$ alkoxyalkyl, $C_{1-10}$ hydroxyalkyl, $C_{1-10}$ aminoalkyl, $C_{1-10}$ perfluoroalkyl, $C_{1-10}$ haloalkyl, $C_{1-10}$ carboxyalkyl, $C_{1-10}$ amidoalkyl or $C_{1-10}$ ketoalkyl, $R^2$, $R^3$ are the same or different and each H, $C_{1-4}$ alkyl, $C_{2-4}$ alkenyl, $C_{2-4}$ alkynyl, $C_{1-4}$ alkoxyalkyl, $C_{1-4}$ hydroxyalkyl, $C_{1-4}$ aminoalkyl, $C_{1-4}$ perfluoroalkyl, $C_{1-4}$ haloalkyl, Hal, $C_{1-4}$ carboxyalkyl, OR, SR, NRR, $(CH_2)_n$CONRR, NR(CO)R or $(CH_2)_n CO_2 R$, $R^4$ is a leaving group selected from the group consisting of halogen, $XR^8$, $X(C=X)R^8$, $OSOR^8$, $OSO_2R^8$ $OSO_2Hal$, $SOR^8$, $SO_2R^8$, $SO_2NR^8{}_2$ $NRSO_2R$, $(C=X)R^8$, $(C=X)NR^8{}_2$, $(C=X)R^8$, $NO_2$, CN, $PO_nR^8{}_2$ or $XC_6H_{4-n}Y_n$ Y is the same or different and is R, $NO_2$, Hal, $CONR^8{}_2$, $SO_2NR^8{}_2$ or $CO_2R$, $R^5$ is R or $R^4$ R is the same or different and is H, $C_{1-4}$ alkyl, $C_{2-4}$ alkenyl, $C_{2-4}$ alkynyl, $C_{1-4}$ alkoxy, $C_{1-4}$ alkoxyalkyl, $C_{1-4}$ hydroxyalkyl, $C_{1-4}$ aminoalkyl, $C_{1-4}$ perfluoroalkyl, $C_{1-4}$ haloalkyl or $C_{1-4}$ carboxyalkyl, whereby two or more of the groups $R^1$, $R^2$, $R^3$, $R^4$ and $R^5$ may be combined to form a substituted or unsubstituted carbocyclic or heterocyclic ring which may be saturated or unsaturated, wherein the β-lactam contains or has covalently bonded thereto at least one detectable moiety, and with the proviso that when $R^4$ is $XR^8$, X is S and $R^1$ and $R^4$ are combined to form a cyclic carboxyalkyl group, then the detectable moiety is not $^{125}I$.

7. The labelled HLE inhibitor of claim 4 where the inhibitor is an azetidinone.

8. The labelled HLE inhibitor of claim 7 where the azetidinone has the formula:

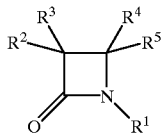

wherein $R^1$ is $R^8$, $XR^8$, $(CRR)_n(C=X)R^8$ or $(C=X)NR^8{}_2$

X is O or S n is 0-3, $R^8$ is H, OH, a substituted or unsubstituted $C_{3-12}$ carbocyclic or heterocyclic ring which may be saturated or unsaturated, $C_{1-10}$ alkyl, $C_{3-12}$ aryl, $C_{4-12}$ alkylaryl, $C_{2-10}$ alkenyl, $C_{2-10}$ alkynyl, $C_{1-10}$ alkoxy, $C_{1-10}$ alkoxyalkyl, $C_{1-10}$ hydroxyalkyl, $C_{1-10}$ aminoalkyl, $C_{1-10}$ perfluoroalkyl, $C_{1-10}$ haloalkyl, $C_{1-10}$ carboxyalkyl, $C_{1-10}$ amidoalkyl or $C_{1-10}$ ketoalkyl, $R^2$, $R^3$ are the same or different and each H, $C_{1-4}$ alkyl, $C_{2-4}$ alkenyl, $C_{2-4}$ alkynyl, $C_{1-4}$ alkoxyalkyl, $C_{1-4}$ hydroxyalkyl, $C_{1-4}$ aminoalkyl, $C_{1-4}$ perfluoroalkyl, $C_{1-4}$ haloalkyl, Hal, $C_{1-4}$ carboxyalkyl, OR, SR, NRR, $(CH_2)_nCONRR$, $NR(CO)R$ or $(CH_2)_nCO_2R$, $R^4$ is a leaving group selected from the group consisting of halogen, $XR^6$, $X(C=X)R^8$, $OSOR^8$, $OSO_2R^8$ $OSO_2Hal$, $SOR^8$, $SO_2R^8$, $SO_2NR^8{}_2$ $NRSO_2R$, $(C=X)R^8$, $(C=X)NR^8{}_2$, $(C=X)R^8$, $NO_2$, CN, $PO_nR^8{}_2$ or $XC_8H_{4-n}$, Y is the same or different and is R, $NO_2$, halogen, $CONR^8{}_2$, $SO_2NR^8{}_2$ or $CO_2R$, $R^5$ is R or $R^4$ R is the same or different and is H, $C_{1-4}$ alkyl, $C_{2-4}$ alkenyl, $C_{2-4}$ alkynyl, $C_{1-4}$ alkoxy, $C_{1-4}$ alkoxyalkyl, $C_{1-4}$ hydroxyalkyl, $C_{1-4}$ aminoalkyl, $C_{1-4}$ perfluoroalkyl, $C_{1-4}$ haloalkyl or $C_{1-4}$ carboxyalkyl, wherein the azetidinone contains or has covalently bonded thereto at least one detectable moiety.

9. The labelled HLE inhibitor of claim 8 where the detectable moiety is attached at the $R_1$ position.

10. The labelled HLE inhibitor of claim 8 where at least one of the groups $R_{1-5}$ bears an amine substituent.

11. A method for detecting a site of inflammation in vivo comprising:

administering the labelled HLE inhibitor of claim 1;

detecting the presence of the HLE inhibitor at a site of inflammation.

12. A method for labelling leucocytes in vitro comprising:

combining leucocytes and the labelled HLE inhibitor of claim 1.

13. A method for imaging thromb in vivo comprising:

administering the labelled HLE inhibitor of claim 1;

detecting radiation emitted by the labelled HLE inhibitor that has accumulated at a thromb and generating an image therefrom.

14. A method for treating arthritis, bone infection or other hyperproliferative disease with radiation, the method comprising:

administering the labelled HLE inhibitor of claim 1.

* * * * *

UNITED STATES PATENT AND TRADEMARK OFFICE
CERTIFICATE OF CORRECTION

PATENT NO. : 6,375,926 B1
DATED : April 23, 2002
INVENTOR(S) : Barnes et al.

It is certified that error appears in the above-identified patent and that said Letters Patent is hereby corrected as shown below:

<u>Title page,</u>
Item [57], ABSTRACT,
Line 6, please delete "rthritis" and insert therefor -- arthritis --.

<u>Column 48,</u>
Line 8, please delete "$XC_6H_{4-n}Y_n$" and insert therefore -- $XC_8H_{4-n}Y_n$ --.

Signed and Sealed this

Fourth Day of March, 2003

JAMES E. ROGAN
*Director of the United States Patent and Trademark Office*